(12) United States Patent
Mizuno et al.

(10) Patent No.: US 6,569,084 B1
(45) Date of Patent: May 27, 2003

(54) ENDOSCOPE HOLDER AND ENDOSCOPE DEVICE

(75) Inventors: Hitoshi Mizuno, Koganei (JP); Yuichi Ikeda, Tama (JP); Toshimasa Kawai, Hachioji (JP); Toshinari Maeda, Hachioji (JP); Koji Takamura, Sagamihara (JP); Keiichi Arai, Hachioji (JP); Raifu Matsui, Hino (JP); Atsushi Amano, Tama (JP); Kazuhiko Arai, Hachioji (JP); Hiroyuki Fukuda, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/536,403

(22) Filed: Mar. 28, 2000

(30) Foreign Application Priority Data

| Mar. 31, 1999 | (JP) | 11-093794 |
| Mar. 31, 1999 | (JP) | 11-093795 |
| Mar. 31, 1999 | (JP) | 11-093796 |

(51) Int. Cl.⁷ .................................................. A61B 1/00
(52) U.S. Cl. ........................ 600/102; 600/146; 248/325
(58) Field of Search ................................ 600/102, 101, 600/146, 149, 145; 606/130; 248/176.1, 186.1, 186.2, 317, 324, 325

(56) References Cited

U.S. PATENT DOCUMENTS

| 3,566,872 A | * | 3/1971 | Draeger et al. | 128/897 |
| 4,617,915 A | * | 10/1986 | Arakawa | 600/102 |
| 4,854,301 A | | 8/1989 | Nakajima | |
| 5,159,446 A | * | 10/1992 | Hibino et al. | 348/65 |
| 5,184,601 A | * | 2/1993 | Putman | 312/209 |
| 5,243,967 A | * | 9/1993 | Hibino | 348/65 |
| 5,259,365 A | * | 11/1993 | Nishikori et al. | 5/600 |
| 5,490,652 A | * | 2/1996 | Martin | 248/282.1 |
| 5,531,664 A | * | 7/1996 | Adachi et al. | 600/152 |
| 5,876,325 A | * | 3/1999 | Mizuno et al. | 600/102 |
| 6,102,850 A | * | 8/2000 | Wang et al. | 414/2 |

FOREIGN PATENT DOCUMENTS

| JP | 63-194659 | 8/1988 |
| JP | 6-30891 | 2/1994 |

* cited by examiner

*Primary Examiner*—John P. Leubecker
(74) *Attorney, Agent, or Firm*—Frishauf, Holtz, Goodman & Chick, P.C.

(57) ABSTRACT

An endoscope device is provided which includes a manipulation portion and an inserted portion connected thereto, and an endoscope holder is provided at an elevated position, for example, on a ceiling. The endoscope device is rotatably suspended from the endoscope holder with its inserted portion extending downward. The endoscope holder has an endoscope manipulation unit for operating the endoscope device and peripheral equipment.

19 Claims, 15 Drawing Sheets

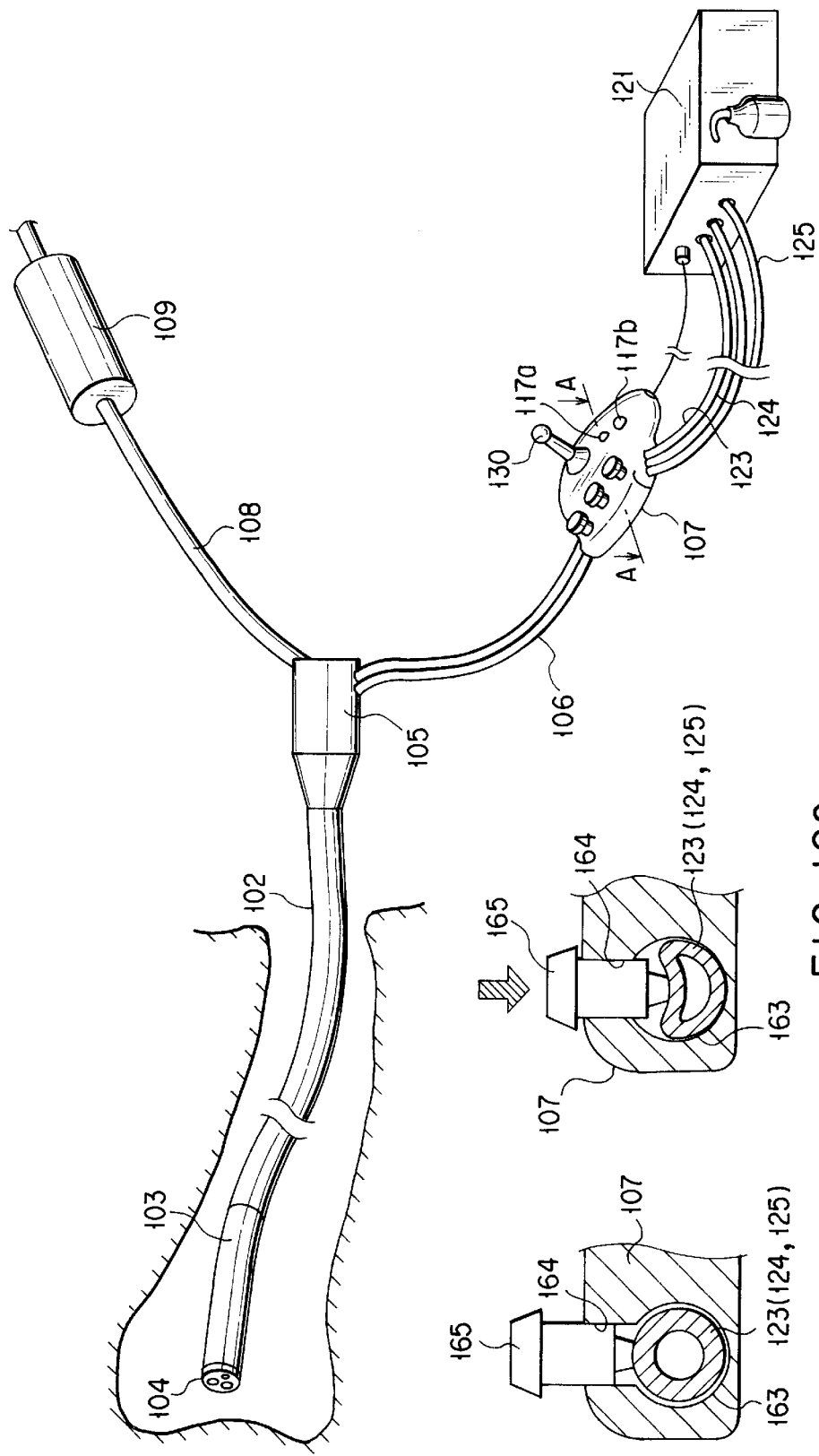

ENDOSCOPE HOLDER AND ENDOSCOPE DEVICE

CROSS-REFERENCE TO RELATED APPLICATIONS

This application is based upon and claims the benefit of priority from the prior Japanese Patent Applications No. 11-093794, filed Mar. 31, 1999; No. 11-093795, filed Mar. 31, 1999; and No. 11-093796, filed Mar. 31, 1999, the entire contents of which are incorporated herein by reference.

BACKGROUND OF THE INVENTION

The present invention relates to an endoscope device and an endoscope holder for use in medical or industrial applications.

For example, a medical endoscope will be explained. A medical endoscope has a manipulation portion provided at a proximal end of an elongate inserted portion and having a curving manipulation portion for curving a curved portion provided close to a distal end of the inserted portion. In addition, a tip-constituting portion of the inserted portion has an illumination or observation window formed therein and a nozzle formed therein for feeding an air or water.

The inserted portion internally has a signal line to which an illuminating optical system or image pickup element is connected, an air and water supply tube in communication with the nozzle, and a forceps channel for suction or insertion of a treatment instrument or the like.

The illuminating optical system and the signal line are each connected to a light source video unit operating as an external device, via a universal cable connected to the manipulation portion, and the air and water supply tube and the forceps channel are each connected to an air and water supply and suction unit. In addition, the forceps channel is in communication with a treatment instrument insertion port formed in the manipulation portion.

In order to observe and treat the inside of a body cavity, a standing operator grips the manipulation portion with the left hand, while holding the inserted portion in the right hand to insert it into the body cavity. While observing the inside of the cavity using a monitor or the like, the operator manipulates the curving manipulation portion to curve the curved portion, operates an air and water supply and suction button, or inserts the treatment instrument into the forceps channel through the treatment instrument insertion port to gather tissues as required.

In this case, the operator must perform manipulations while holding the manipulation portion of the endoscope in the left hand, that is, holding the weight of the inserted portion connected to the manipulation portion, so that the operator's left arm is likely to be fatigued. This is a heavy burden on the operator if the observation and treatment requires a large amount of time.

In order to solve such a problem, for example, Japanese Unexamined Patent Application Publication (Tokkai-Sho) No. 63-194659 provides an endoscope control box in a chair in which the operator sits, and connects the universal cable for the endoscope to the endoscope control box so that the operator can hold the manipulation portion of the endoscope and insert the inserted portion into the body cavity for observations and treatments while sitting in the chair, thereby alleviating the operator's fatigue.

However, although Japanese Unexamined Patent Application Publication (Tokkai-Sho) No. 63-194659 can reduce the operator's burden in that the operator can manipulate the endoscope while sitting in the chair, this is the same as typical endoscope manipulations in that the operator grips the manipulation portion with the left hand, while holding the inserted portion in the right hand to insert it into the body cavity. Thus, this application cannot relieve the operator's fatigue. In addition, the endoscope control box in the endoscope control box is disadvantageous in that cords or tubes must be placed around the chair in which the operator sits, thereby obstructing the operator or an assistant such as a nurse.

In addition, in order to solve the above problem, for example, Japanese Unexamined Patent Application Publication (Tokkai-Hei) No. 6-30891 provides a branched portion at a connection between the manipulation portion and the inserted portion and connects the universal cord to the branched portion so that a light guide, a suction channel, and an air and water supply channel can be inserted through the universal cord, thereby reducing the size and weight of the manipulation portion to ease the operator's fatigue.

Japanese Unexamined Patent Application Publication (Tokkai-Hei) No. 6-30891 is a structure in which the universal cord with the light guide, the suction channel, the air and water supply channel, etc. is connected to the branched portion provided at the connection between the manipulation portion and the inserted portion, thereby reducing the size and weight of the manipulation portion to some degree. However, when the operator holds the manipulation portion in the left hand, the weights of the manipulation and inserted portions and the universal cord are placed on the operator's left arm, so that the operator's left arm is likely to be fatigued. This is a heavy burden on the operator if the observation and treatment requires a large amount of time, whereby this application cannot relieve the operator's fatigue.

In addition, to lessen the cumbersomeness of the manipulation performed by the operator to curve the curved tube portion in order to improve the curving manipulation, a motor-operated curved endoscope has been proposed which curves the curved tube portion of the inserted portion using the driving force of an electric motor.

The motor-operated curved endoscope generally has an angle wire located in the inserted portion so that a pulley with the angle wire laid around it can be rotatively driven to draw the angle wire to curve the curved tube portion. In addition, a rotary encoder is mounted on a shaft portion of the electric motor to detect the angle of the curve based on an output signal from the rotary encoder in order to control the operation of the electric motor so as to curve the curved tube portion up to a predetermined curving angle.

According to the conventional curving method, the angle through which the curved tube portion is curved is determined by the traction movement of the angle wire, which is located in the inserted portion. The angle wire, however, is inserted through a coil sheath located inside the elongate inserted portion and is guided up to a tip of the curved tube portion, so that it moves in sliding contact with an inner surface of the coil sheath during traction, and is subjected to a frictional force from the coil sheath. In particular, when the coil sheath is bent, the angle wire is pressed hard against the inner surface of the coil sheath when moving in sliding contact therewith, and it is thus subjected a larger frictional force.

In general, the inserted portion and the coil sheath are correspondingly bent, and the shapes of the coil sheath and the inserted portion vary correspondingly. Consequently, during the use of the endoscope, the coil sheath is bent into various complicated forms in a fashion corresponding to the inserted portion, and the frictional force received by the angle wire, which is in sliding contact with the coil sheath, varies with its shape. In this manner, the angle wire undergoes a tension that varies with the frictional force it receives, so that it may be elongated to some degree and its locational relationship with the coil sheath may vary. On the other hand, a large compressive force is applied to the coil sheath as reaction to the tension exerted on the angle wire, whereby a certain degree of compressive deformation or distortion is actually inevitable. In addition, in curving the curved tube portion, the traction force to be applied to the angle wire may also vary depending on the amount of external loads on the inserted portion, resulting in the varying tension of the angle wire and the varying frictional or compressive force on the coil sheath.

As described above, in curving the curved tube portion, due to the frictional force applied to the angle wire by the coil sheath or for another reason, an angle down phenomenon may occur in which the amount of curving manipulation using the angle wire decreases to diminish the amount of curving below a required amount.

As a result, the curving angle of the curved tube portion, which is an output value relative to an input value for the electric motor, does not always follow this input value and may vary depending on the curvature of the inserted portion.

In order to solve the above problem, a motor-operated curved endoscope has been contemplated which has an angle wire displacement sensor provided in the inserted portion for detecting the displacement of the angle wire in order to use this vale as control information or to feed back angle wire displacement information to angle manipulation means.

With such an endoscope, however, when the angle manipulation means is used to curve the curved tube portion, the angle wire may be subjected to tension and it cannot be determined whether the tension is due to the angle manipulation or an external force occurring when the curved tube portion collides against a certain object.

BRIEF SUMMARY OF THE INVENTION

It is an object of the present invention to provide an endoscope holder and an endoscope device that can be easily manipulated and that enables the operator's fatigue to be alleviated.

Further, it is another object of the present invention to provide an endoscope device that can independently detect the curving angle of a curved tube portion and an external force applied to the curved tube portion to accurately determine the conditions of the curved tube portion, wherein the device can be easily manipulated.

According to claim 1, an endoscope holder is provided which comprises an endoscope holding portion for rotatably supporting holding an endoscope with its inserted portion extending downward, and holding means for suspending and holding the endoscope holding portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 18A is a perspective view of an endoscope device showing a sixteenth embodiment of the present invention;

FIG. 18B is a sectional view taken along line A—A and showing the sixteenth embodiment of the present invention;

FIG. 18C is a sectional view taken along line A—A and showing the sixteenth embodiment of the present invention;

DETAILED DESCRIPTION OF THE INVENTION (First Embodiment)

Each embodiment of the present invention will be described below with reference to the drawings.

Figure 1:
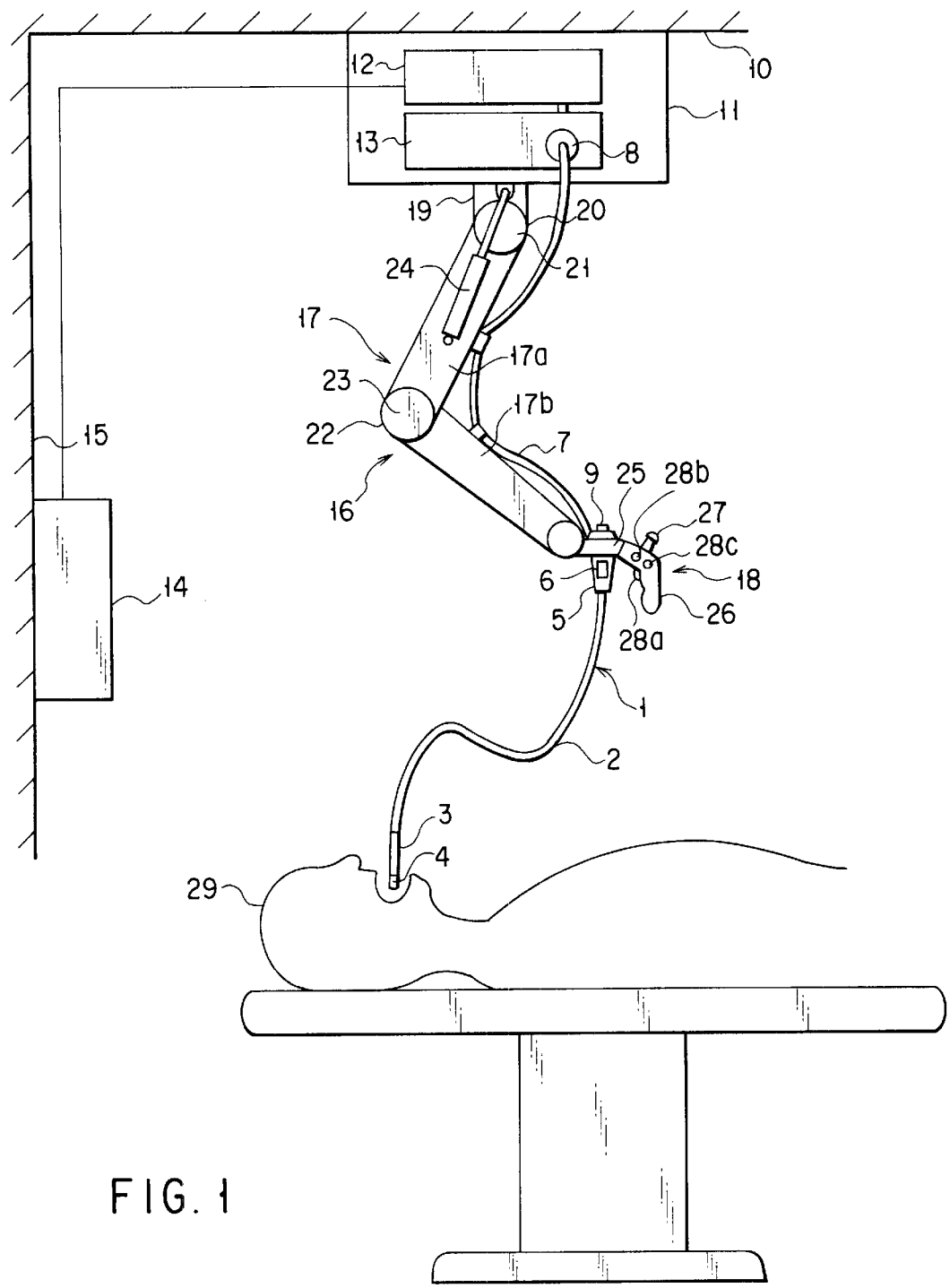
FIG. 1 is a side view of an endoscope device showing a first embodiment of the present invention.

FIG. 1 shows a first embodiment; it is a side view of an endoscope device. A medical endoscope has a tip constituting portion 4 provided at a distal end of a soft elongated inserted portion 2 via a curved portion 3. The inserted portion 2 has a manipulation portion 5 provided at a proximal end thereof and having a built-in actuator 6 for curving the curved portion 3. In addition, the manipulation portion 5 has a universal cable 7 connected thereto and having a connector 8 provided at its tip portion. Further, the manipulation portion 5 has a forceps hole 9 formed at a proximal end thereof.

The inserted portion 2 internally has an illuminating optical system, a signal line connected to a solid image pickup element in the tip constituting portion 4, an angle wire, an air and water supply tube, a forceps channel, etc. (none of them shown).

A control box 11 is provided in a consultating room of a hospital at an elevated position, for example, on a ceiling 10. The control box 11 has a light source video unit 12 and an air and water supply and suction unit 13. The light source video unit 12 has a monitor 14 connected thereto and installed on a wall 15 or the like.

An endoscope holder 16 is fixed to a bottom portion of the control box 11. The endoscope holder 16 is comprised of an articulated arm 17 and an endoscope manipulation unit 18. The control box 11 has a rotating support portion 19 provided on its bottom portion and which can rotate around a vertical axis. The rotating support portion 19 has a first arm 17a of the articulated arm 17 rotatably pivotably supported thereon via a first joint portion 20 and having an electromagnetic clutch brake 21.

The first arm 17a has a second arm 17b rotatably pivotably supported at a lower end thereof via a second joint portion 22 also having an electromagnetic clutch brake 21. Further, a gravity balancer 24 is provided between the first arm 17a of the articulated arm 17 and the rotating support portion 19 so that the articulated arm 17 will not lower inadvertently even when the electromagnetic clutch brake 21 is released.

In addition, the second arm 17b has an endoscope holding portion 25 provided at a lower end thereof.

The endoscope holding portion 25 can rotatably hold the manipulation portion 5 around its axis with the inserted potion 2 of the endoscope 1 suspended downward. The endoscope holding portion 25 has the endoscope manipulation unit 18 integrated therewith.

The endoscope manipulation unit 18 includes a grip 26 having a curving manipulation switch 27, an air and water supply switch 28a, a suction switch 28b, and a manipulation switch 28c.

Next, the operation of the first embodiment will be described.

By holding the manipulation portion 5 of the endoscope 1 on the endoscope holding portion 25 of the endoscope holder 16, the inserted portion 2 can be suspended downward. By guiding the universal cable 7 out from the manipulation portion 5 and extending it along the articulated arm 17, and connecting the connector 8 to the air and water supply and suction unit 13, the endoscope 1 is electrically and optically connected to the air and water supply and suction unit 13 and the light source video unit 12.

Typically, for observations or treatments with the endoscope, the operator grips the manipulation portion 5 with the left hand, while holding the inserted portion 2 in the right hand to insert it into a body cavity from the tip constituting portion 4 of the inserted portion 2. Since, however, the endoscope 1 is held by the endoscope holder 16, the operator does not need to hold the endoscope 1 and can insert the inserted potion 2 into the body cavity of a patient 29 simply by holding this portion 2.

With the endoscope manipulation unit 18 in the endoscope holder 16, when the operator grips the grip 26 to operate the manipulation switch 28c to unlock the electromagnetic clutch brakes 21, 23, the first and second joint portions 20, 22 of the articulated arm 17 can be rotatively moved. When the operator depresses the grip 26, the articulated arm 17 is extended to lower the entire endoscope 1, whereas when the operator pulls up the grip 26, the articulated arm 17 is contracted to elevate the entire endoscope 1. In addition, by gripping and swinging the grip 26 in a lateral direction of the operator, the entire endoscope 1 can be pivoted around the rotating support section 19 so as to be directed in an arbitrary direction. In addition, the manipulation section 5 of the endoscope 1 is rotatably held on the endoscope holding section 25, so that the entire endoscope 1 can be rotated by gripping and twisting the inserted portion 2.

In addition, the curving manipulation switch 27 can be operated to curve the curved portion 3, and the air and water supply switch 28a and the suction switch 28b can be operated to feed or suck an air or water. In addition, a forceps can be inserted through the forceps hole 9 to gather tissues or the like as required.

In this manner, the entire endoscope 1 is held by the endoscope holder 16 and supported by the articulated arm 16 with the gravity balancer 24, thereby eliminating the need to manually hold the endoscope 1 and requiring only a small amount of force for manipulations to ease the operator's fatigue. In addition, the operator can use both hands to operate the inserted portion 2 and the various switches, so that the manipulability of the endoscope can be improved. Further, since the endoscope holder 16 and the various cables and tubes are located at elevated positions, movement of the operator and nurses is prevented from being obstructed and the consultating room can be kept clean.

(Second Embodiment)

Figure 2:
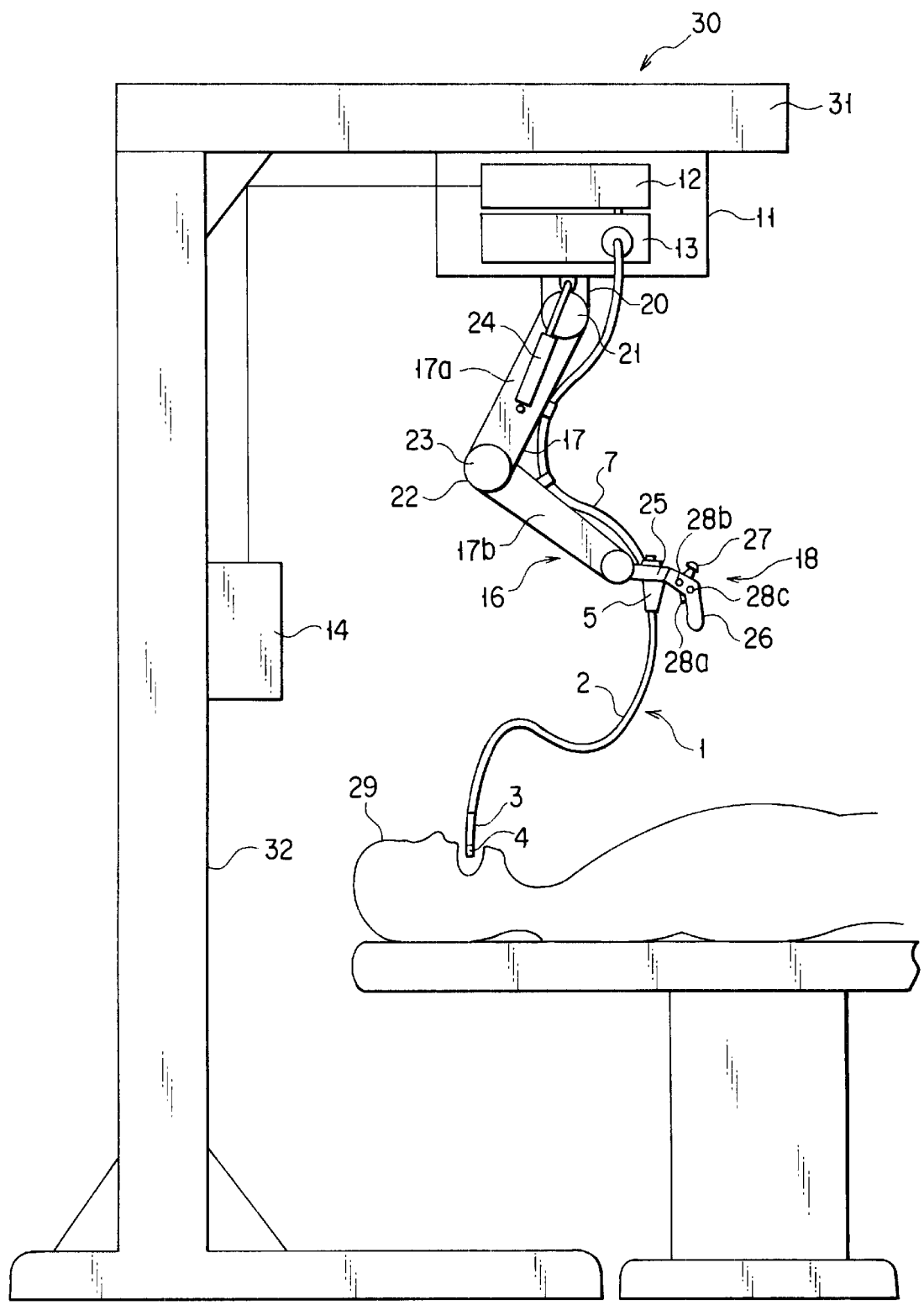
FIG. 2 is a side view of an endoscope device showing a second embodiment of the present invention.

FIG. 2 shows a second embodiment. The same components as in the first embodiment have the same reference numerals, and description thereof is omitted. According to this embodiment, the control box 11 is provided on a horizontal portion 31 of a frame 30, while a monitor 14 is provided on a vertical portion 32 thereof, and the remaining part of this configuration is the same as in the first embodiment. This embodiment eliminates the needs for work for installing the control box on the ceiling and easily accommodates a change in installation site.

(Third Embodiment)

Figure 3:
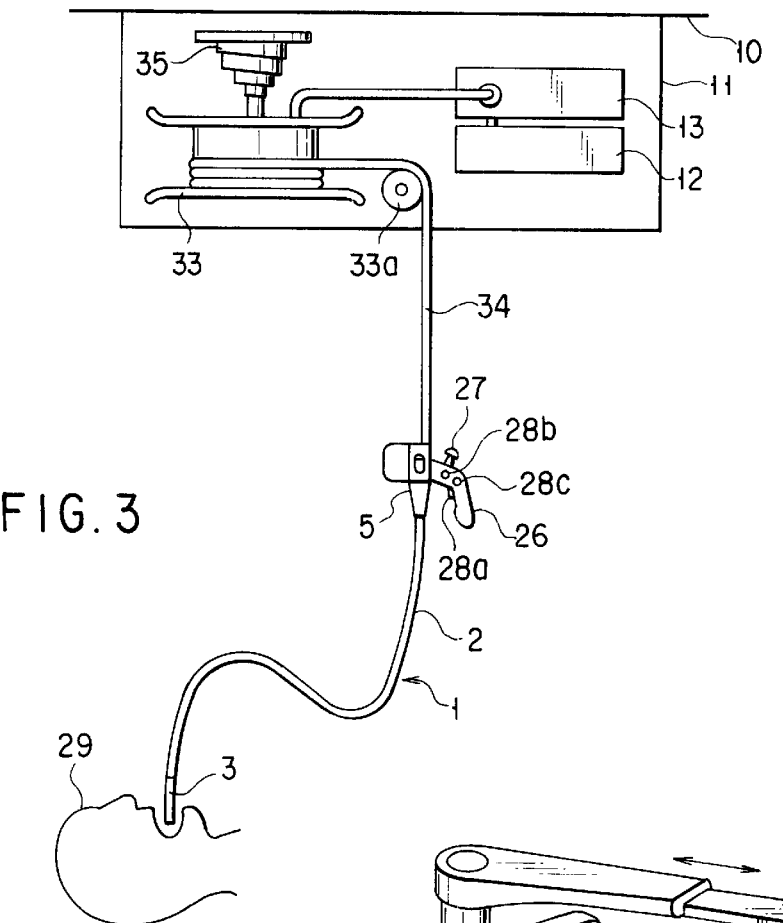
FIG. 3 is a side view of an endoscope device showing a third embodiment of the present invention.

FIG. 3 shows a third embodiment. The same components as in the first embodiment have the same reference numerals, and description thereof is omitted. According to this embodiment, a control box 11 fixed to a ceiling 10 has a housing device 33 in the form of a rotating drum provided inside and around which a flexible tube 34 is wound. The flexible tube 34 has light guide fibers, a signal line, and an air and water supply and suction tube (not shown) installed inside.

Further, the flexible tube 34 has a proximal end connected to a light source video unit 12 and an air and water supply and suction unit 13 and has a dismal end connected to a manipulation portion 5 of an endoscope. Thus, the endoscope 1 is suspended via the flexible tube 34, and the housing device 33 has a gravity balancer 35 for preventing the endoscope 1 from falling due to the weight thereof and urging the flexible tube 34 in a winding direction.

The remaining part of this configuration is the same as in the first embodiment. According to this embodiment, when the operator holds and depresses a grip 26, the hosing device 33 rotates to deliver the flexible tube 34, whereas when the operator lifts the grip 26, the flexible tube 34 is wound around the housing device 33. Consequently, this embodiment provides effects similar to those of the first embodiment.

(Fourth Embodiment)

Figure 4:
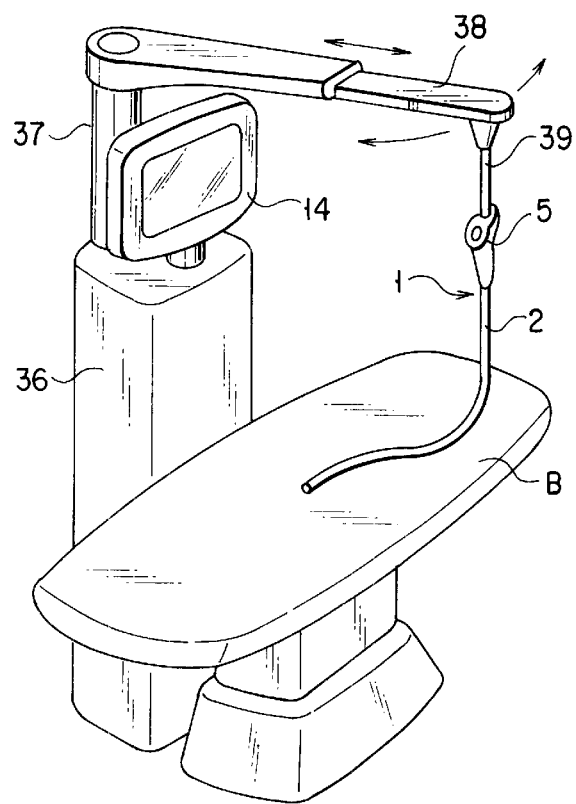
FIG. 4 is a perspective view of an endoscope device showing a fourth embodiment of the present invention.

FIG. 4 shows a fourth embodiment. The same components as in the first embodiment have the same reference numerals, and description thereof is omitted. According to this embodiment, a floor type control box 36 installed near a bed B has a light source video unit (not shown) and an air and water supply and suction unit (not shown) housed therein.

On the control box 36, a monitor 14 is mounted and a strut 37 is provided in a fashion standing in a vertical direction. The strut 37 has a stretchable arm 38 provided at an upper end portion thereof for rotative movement within a horizontal plane, and the stretchable arm 38 has an endoscope holder 39 provided at its tip portion. The endoscope holder 39 holds a manipulation portion 5 of an endoscope 1, from which an inserted portion 2 is suspended downward.

The manipulation portion of the endoscope is connected to a light source video unit and an air and water supply and suction unit both provided in the control box 36, via light guide fibers, a signal line, and an air and water supply and suction tube (not shown) installed both inside the stretchable arm 38 and inside the strut 37.

Thus, when the operator grips the manipulation portion 5 to rotatively move it in a lateral direction of the operator, the stretchable arm 38 rotatively move around the strut 37. When the operator pushes or pulls the manipulation portion 5 in a longitudinal direction of the operator, the stretchable arm 38 is contracted or stretched to enable the endoscope 1 to move to an arbitrary position. Accordingly, the manipulability of the endoscope 1 can be improved. The remaining part of the configuration and operation is the same as in the first embodiment, so that this embodiment provides effects similar to those of the first embodiment.

(Fifth Embodiment)

Figures 5, 6:
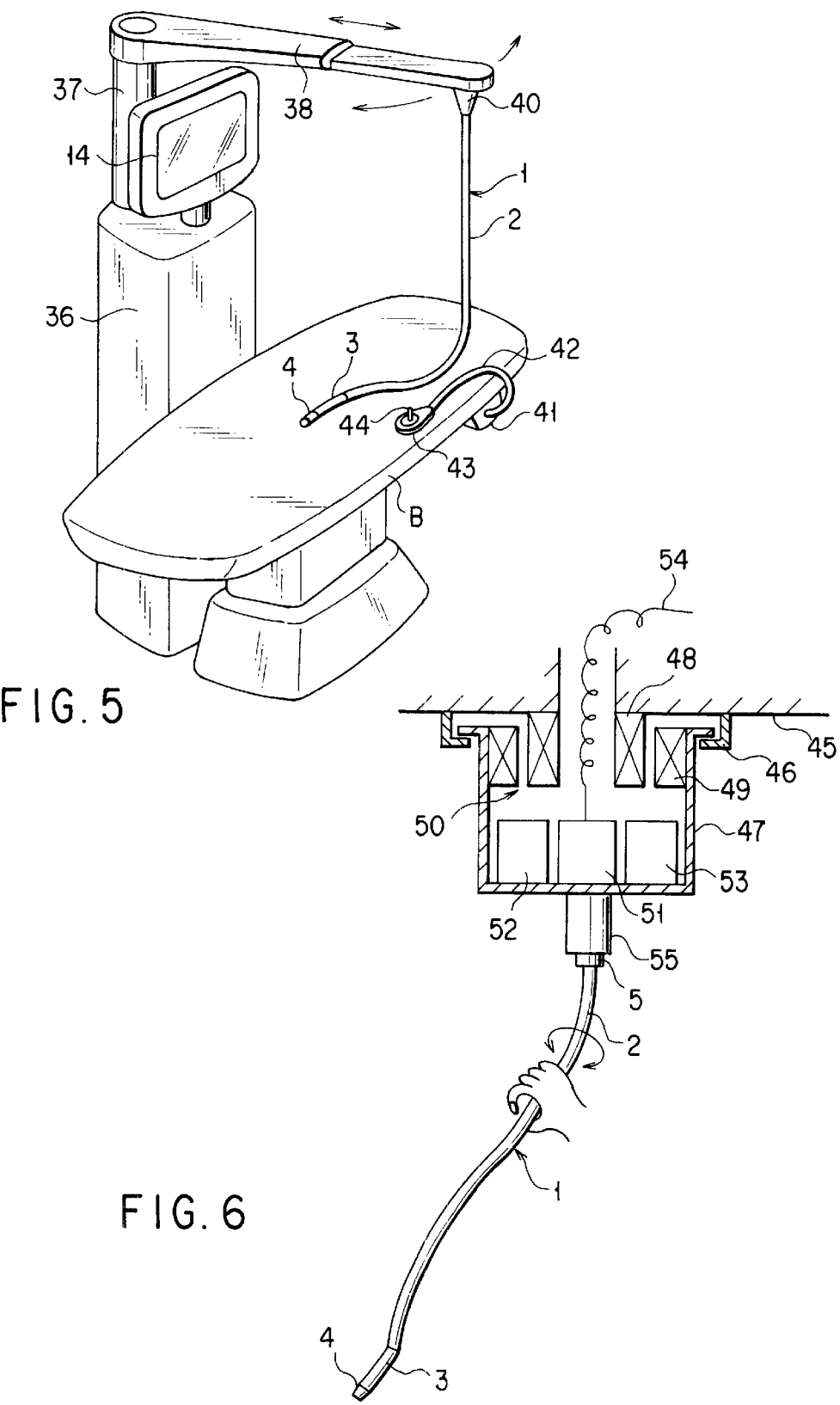
FIG. 5 is a perspective view of an endoscope device showing a fifth embodiment of the present invention.
FIG. 6 is a vertical sectional view of an endoscope device showing a sixth embodiment of the present invention.

FIG. 5 shows a fifth embodiment. The same components as in the first and fourth embodiments have the same reference numerals, and description thereof is omitted. According to this embodiment, a proximal end portion 40 of an endoscope 1 is fixed to a tip portion of a stretchable arm 38, and the endoscope 1 is suspended in such a manner that its inserted portion 2 extends downward. The proximal end portion 40 has a built-in actuator (not shown) for curving a curved portion 3 of the inserted portion 2.

A bed B includes a terminal box 41 having a manipulation portion 43 that acts as manipulation means via a cord 42. The manipulation portion 43 has a curving manipulation switch 44, an air and water supply switch, a suction switch, and a manipulation switch (the latter three switches are not shown) that all control the actuator.

Thus, by inserting the inserted portion 2 into the patient's body cavity and holding the manipulation portion 43 to operate the curving manipulation switch 44, the air and water supply switch, the suction switch, and the manipulation switch, the operator can remote-control the endoscope 1 and peripheral equipment such as a light source video unit and an air and water supply and suction unit. Consequently, the manipulability of the endoscope can be improved. The remaining part of the configuration and operation is the same as in the first and fourth embodiments, so that this embodiment provides effects similar to those of the first and fourth embodiments.

(Sixth Embodiment)

FIG. 6 shows a fourth embodiment; it is a vertical sectional side view of an endoscope holder. An elevated mounting portion 45 such as a ceiling or a frame has a support ring 46 fixed thereto and on which a cylindrical control box 47 is rotatably supported. The support ring 46 has a stator 48 fixed to the elevated mounting portion 45 in an axial portion thereof, and the stator 48 has a rotor 49 provided in its outer periphery and fixed to the control box 47. The stator 48 and the rotor 49 constitute a motor 50.

The control box 47 has a light source video unit 51, an air and water supply unit 52, and a suction unit 53 provided inside and connected to a power supply via a looped cord 54. The control box 47 has a manipulation portion 5 of an endoscope 1 fixed to a bottom surface thereof in its axial portion, and the endoscope 1 is suspended from the control box 47 with an inserted portion 2 extending downward.

The manipulation portion 5 has a built-in actuator (not shown) for curving-a curved portion 3 of the inserted portion 2, and also has switches such as a curving manipulation switch, an air and water supply switch, a suction switch, and a manipulation switch (none of them shown).

According to this embodiment, when the operator holds the inserted portion 2 of the endoscope 1 to insert it into the patient's body cavity or after this insertion, a rotation torque T occurring when the inserted portion 2 is gripped and twisted is measured using a torque sensor 55. If the measured value does not meet a preset threshold torque Tthre, that is, if −Tthre<T<Tthre is not met, then the rotor 49 can be rotated in a direction in which the torque decreases, by feedback-controlling the rotor 49 relative to the stator 48 by an amount of current proportional to T−Tthre. Consequently, the load torque occurring when the operator twists the endoscope 1 can be reduced to improve the manipulability of the endoscope.

(Seventh Embodiment)

Figure 7:
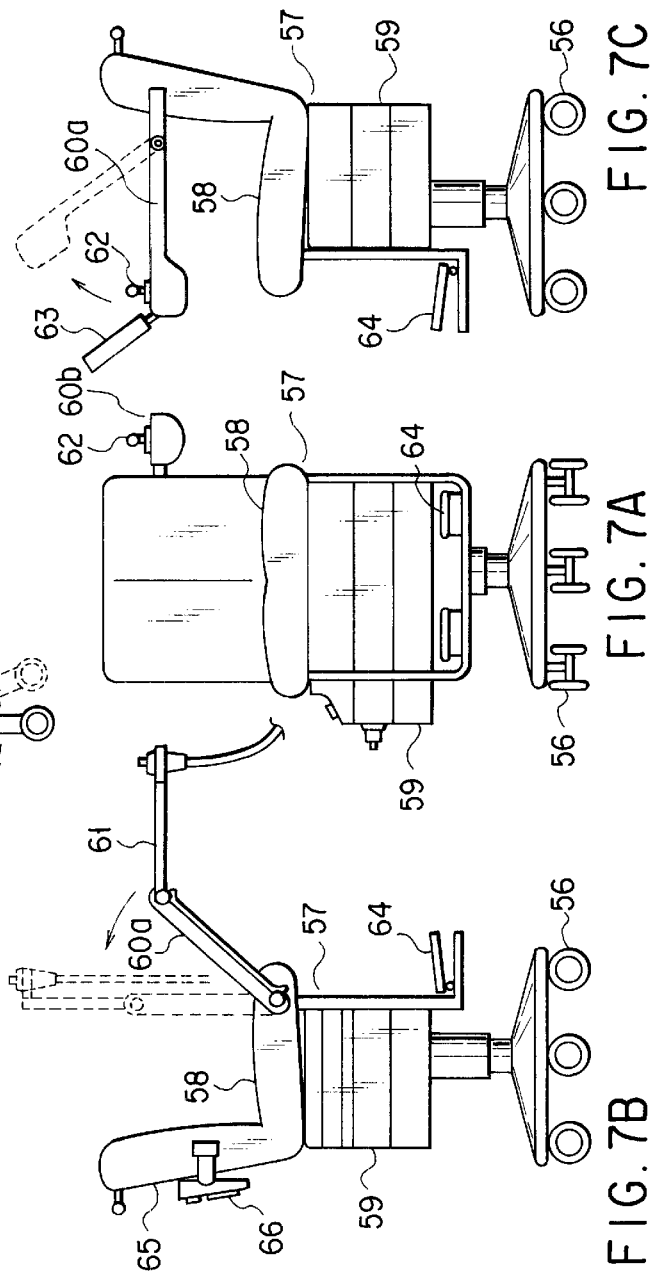
FIG. 7A is a front view of an endoscope device showing a seventh embodiment of the present invention.
FIG. 7B is a left side view of the endoscope device showing the seventh embodiment of the present invention.
FIG. 7C is a right side view of the endoscope device showing the seventh embodiment of the present invention.
FIG. 7D is a top view of the endoscope device showing the seventh embodiment of the present invention.

FIGS. 7A to 7D show a seventh embodiment. The same components as in the first embodiment have the same reference numerals, and description thereof is omitted. FIG. 7A is a front view, FIG. 7B is a left side view, FIG. 7C is a right side view, and FIG. 7D is a top view. A control box 59 is provided under a seat portion 58 of a chair body 57 having casters 56. The control box 59 has a light source video unit and an air and water supply and suction unit (neither of them shown) provided inside.

One 60a of the armrest portions of the chair body 57 has an endoscope holder 61, and as in the fifth embodiment, the endoscope holder 61 holds a proximal end portion 40 of an endoscope 1 suspended with its inserted portion 2 extending downward. The other armrest portion 60b of the chair body 57 has an endoscope manipulation portion 62 and a small-sized display 63. Furthermore, the chair body 57 has a foot switch 64 that can elevate and lower the seat portion 58 and operate peripheral equipment. In addition, a backrest portion 65 of the chair body 57 has a keyboard 66 for inputting data to the endoscope 1.

Thus, by inserting the inserted portion 2 into the patient's body cavity and operating a curving manipulation switch, air and water supply switch, and suction switch on the endoscope manipulation portion 62, the operator can remote-control the endoscope 1 and peripheral equipment such as a light source video unit and an air and water supply and suction unit. Consequently, the manipulability of the endoscope can be improved. The remaining part of the configuration and operation is the same as in the first embodiment, so that this embodiment provides effects similar to those of the first embodiment.

(Eighth Embodiment)

Figure 8:
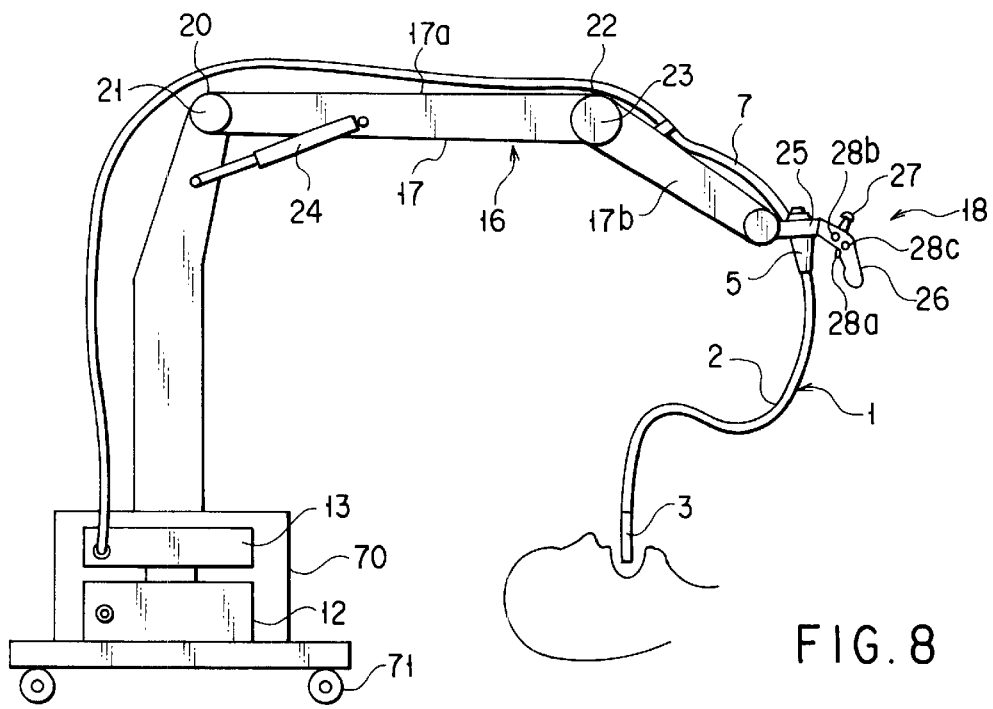
FIG. 8 is a side view of an endoscope device showing an eighth embodiment of the present invention.

FIG. 8 shows an eighth embodiment. The same components as in the first embodiment have the same reference numerals, and description thereof is omitted. A floor type frame 70 has casters 71 for movement. The frame 70 has a light source video unit 12 and an air and water supply and suction unit 13 housed inside. In addition, the frame 70 has an endoscope holder 16 consisting of an articulated arm 17, and an endoscope holding portion 25 of the endoscope holder 16 holds a manipulation portion 5 of the endoscope 1. The remaining part of the configuration and operation is the same as in the first embodiment, so that this embodiment provides effects similar to those of the first embodiment.

(Ninth Embodiment)

Figure 9:
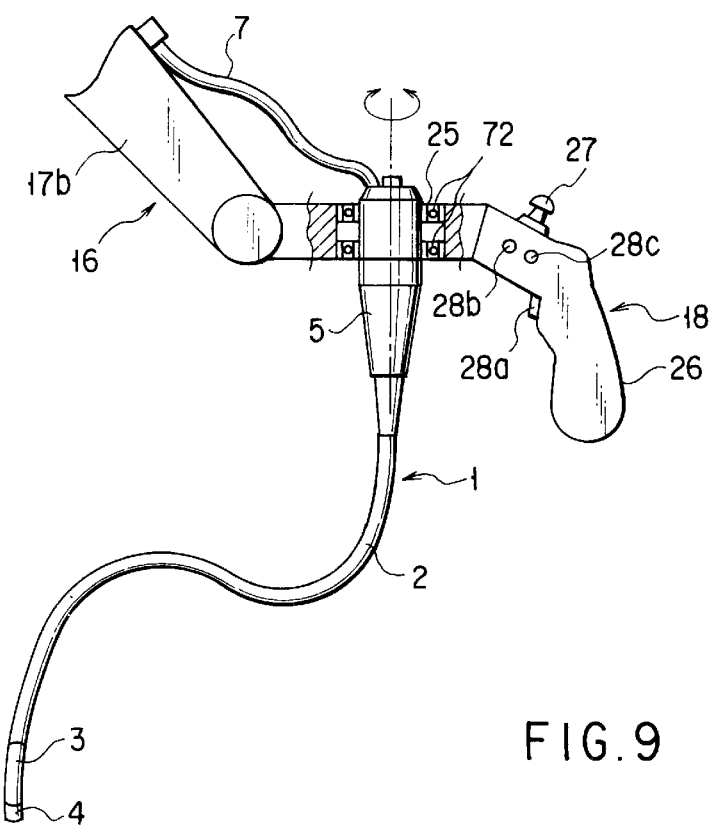
FIG. 9 is a partly cutaway side view of an endoscope holder showing a ninth embodiment of the present invention.

FIG. 9 shows a ninth embodiment. The same components as in the first embodiment have the same reference numerals, and description thereof is omitted. An endoscope holder 16 has an endoscope holding portion 25 rotatably provided at a tip portion thereof via bearings 72 for holding a manipulation portion 5 of an endoscope 1. The endoscope 1 is suspended from the endoscope holding portion with its inserted portion 2 extending downward.

According to this embodiment, when the operator holds the inserted portion 2 of the endoscope 1 to insert it into the patient's body cavity or after this insertion, the manipulation portion 5 is rotated integrally with the inserted portion 2 when the operator grips and twists the inserted portion 2. As a result, the load torque occurring when the operator twists the endoscope 1 can be reduced to improve the manipulability of the endoscope.

(Tenth Embodiment)

Figure 10:
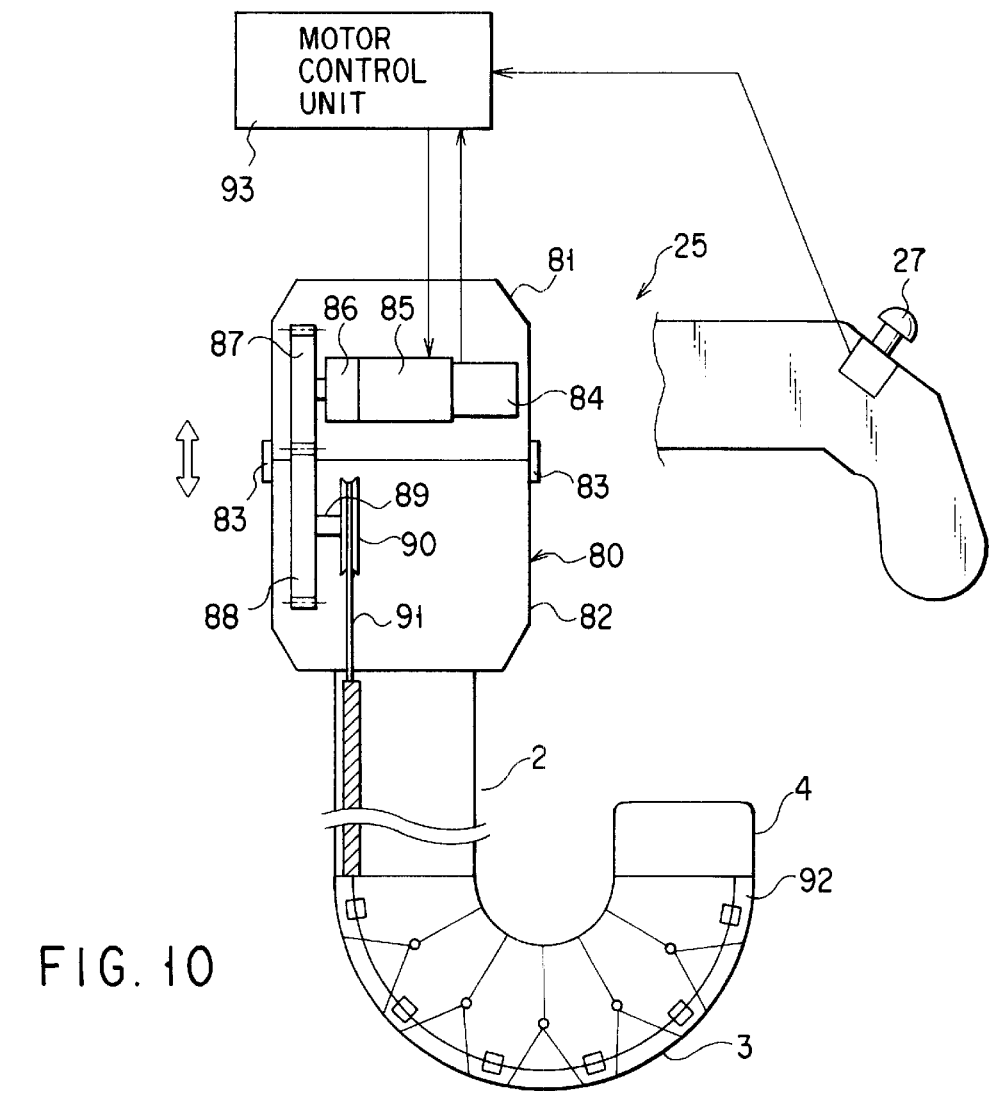
FIG. 10 is a configuration diagram of an endoscope device showing a tenth embodiment of the present invention.

FIG. 10 shows a tenth embodiment. The same components as in the first embodiment have the same reference numerals, and description thereof is omitted. An endoscope holding portion 25 of an endoscope holder 16 holds a manipulation portion 5 of an endoscope 1 suspended therefrom with an inserted portion 2 extending downward. A manipulation portion body 80 of an endoscope 1 is divided into two, that is, a proximal-end side casing 81 and a tip side casing 82 that are coupled together by means of clamps 83. The proximal-end side casing 81 has a motor 85 inside which comprises an encoder 84 and which is linked with a first gear 87 via a speed reducer 86.

The tip side casing 82 has a second gear 88 inside which meshes with the first gear 87 and which includes a rotating shaft 89 having a pulley 90. The pulley 90 has an angle wire 91 laid around it and penetrating the inserted portion 2 so as to connect to a tip curved block 92 of a curved portion 3.

A curving manipulation switch 27 provided on an endoscope holding portion 25 is connected to a motor control unit 93 that obtains information from the encoder 84 to control the rotation of a motor 85.

According to this embodiment, an instructed value indicating a curving angle or a curving speed is transmitted from the curving manipulation switch 27 to the motor control unit 93. The motor control unit 93 transmits a drive signal to the motor 85 in accordance with the instructed value to operate the motor 85, thereby rotating the pulley 90 via the first and second gears 87, 88. The rotation of the pulley 90 pushes or pulls the angle wire 91 to curve the curved portion 3.

The encoder 84 provided in the motor 85 can transmit rotation information on the motor 85 to the motor control unit 93 as encoder information to check whether or not the motor 85 is operating correctly in accordance with the instructed value. Accordingly, the curving manipulation switch 27 can be used to simply and accurately curve the curved portion 3 of the endoscope 1, thereby improving the manipulability of the endoscope.

In addition, in an emergency where the motor 85 stops due to a failure or runs uncontrollably, the manipulation portion body 80 can be separated into the proximal-end side casing 81 and the tip side casing 82 by unlocking the clamp 83. By separating the proximal-end side casing 81 from the tip side casing 82, the first and second gears 87 and 88 are disengaged from each other to block the power of the motor 85. As a result, the second gear 88 can be manually rotated to curve or straighten the curved portion 3, thereby improving safety.

(Eleventh Embodiment)

Figure 11:
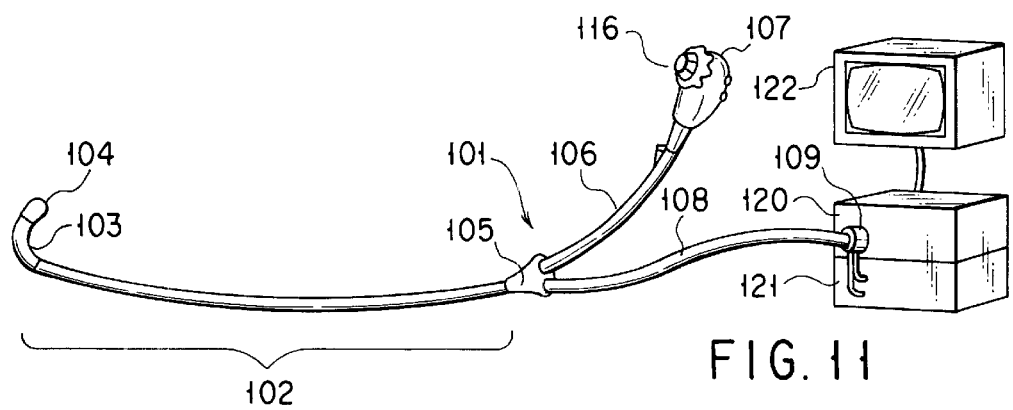
FIG. 11 is a perspective view of an endoscope device showing an eleventh embodiment of the present invention.
Figure 12:
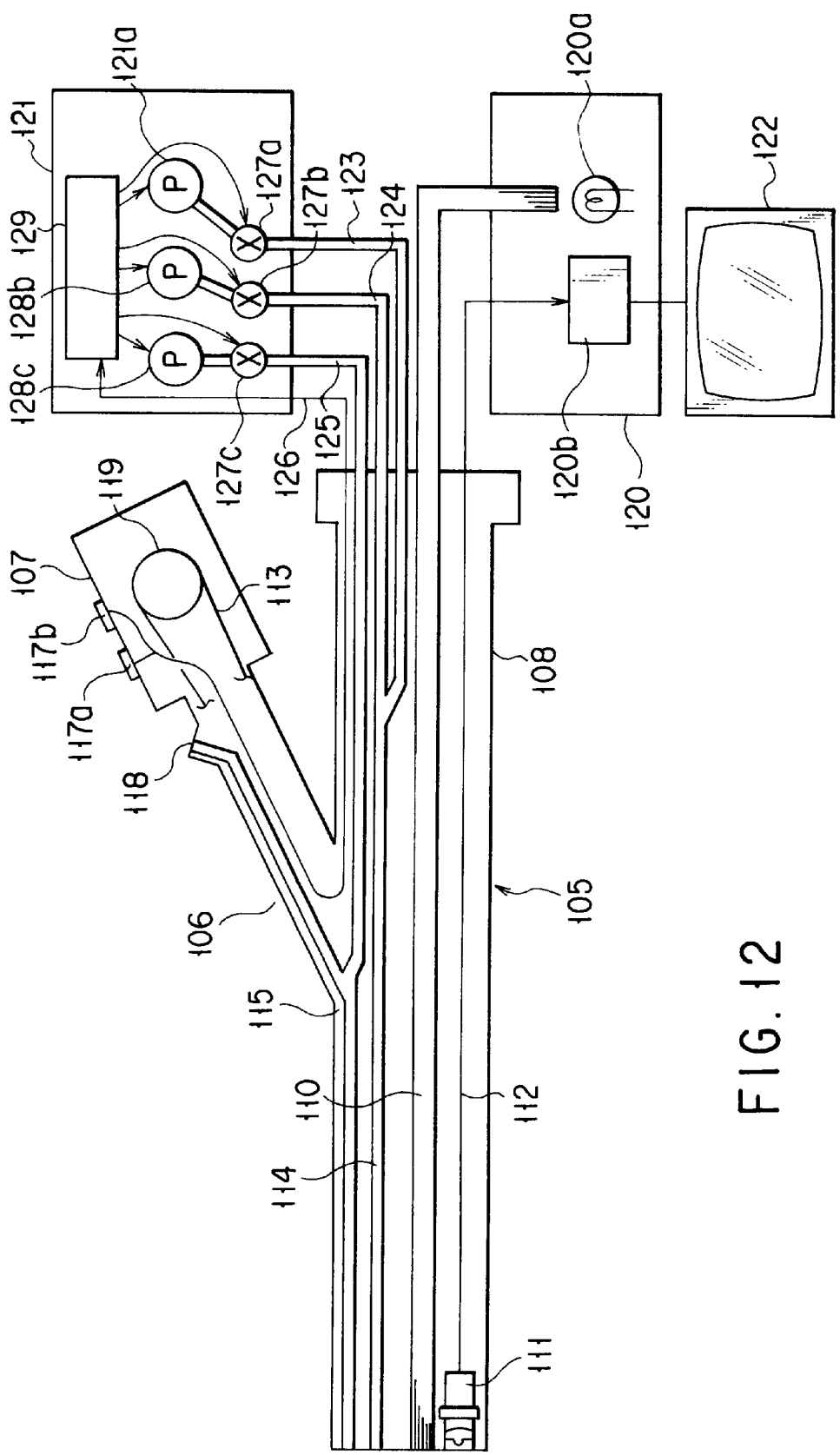
FIG. 12 is a schematic configuration diagram of the endoscope device according to the eleventh embodiment.

FIGS. 11 and 12 show an eleventh embodiment. FIG. 11 is a perspective view of the overall endoscope device, and FIG. 12 is a configuration diagram of the overall endoscope device. A medical endoscope 101 has a tip-constituting portion 104 provided at a distal end of an elongate soft inserted portion 102 via a curved portion 103. The inserted portion 102 has a branched portion 105 at a proximal end thereof, and one of the branches from the branched portion 105 has the manipulation portion 107 connected thereto via a flexible cord 106, while the other branch from the branched portion 105 has a connector 109 connected thereto via a universal cord 108.

The inserted portion 102 has an illuminating optical system 110, a signal like 112 connected to a solid image pickup element 111 of the tip constituting portion 104, an angle wire 113, an air and water supply tube 114, a forceps channel 115, etc. which are all installed inside the inserted portion 102. The manipulation portion 107 has an angle manipulation knob 116 acting as a curving manipulation portion, an air and water supply switch 117a and a suction switch 117b, and a treatment instrument insertion port 118 in communication with the forceps channel 115. The manipulation portion 107 has a rotating drum 119 provided inside and rotated by means of the angle manipulation knob 116, and the angle wire 113 is laid around the rotating drum 119. Thus, the curved portion 103 can be curved by pushing and pulling the angle wire 113. Although one set of the angle wire 113 and the rotating drum 119 are shown, two sets are actually provided to enable the curved portion 103 to be curved both in a vertical and a lateral directions.

Separately from the endoscope 101, a light video unit 120, an air and water supply and suction unit 121, and a monitor 122 are provided as external devices. The light source video unit 120 has the illuminating optical system 110 and the signal line 112 of the solid image pickup element 111 removably connected thereto via the connector 109. There is provided inside the light source video unit 120 a light source 120a opposed to an end surface of the illuminating optical system 110, and a camera control unit 120b connected to the signal line 112 and the monitor 122.

The air and water supply and suction unit 121 has an air supply line 123, a water supply line 124, and a suction line 125 connected thereto and also has a signal line 126 connected thereto which is connected to the air and water supply switch 117a and the suction switch 117b.

The air and water supply and suction unit 121 has a first to a third solenoid valves 127a to 127c inside which are connected to the air supply line 123, the water supply line 124, and the suction line 125 and which are also connected to a first to a third pumps 128a to 128c respectively. Further, the air and water supply and suction unit 121 has a controller 129 provided inside for controlling the first to third solenoid valves 127a to 127c and the first to third pumps 128a to 128c in response to signals from the air and water supply switch 117a and the suction switch 117b.

Next, the operation of the eleventh embodiment will be described.

Typically, for observations or treatments with the endoscope, the operator grips the manipulation portion 107 with the left hand, while holding the inserted portion 102 in the right hand to insert it into a body cavity from the tip constituting portion 104 of the inserted portion 102. At this point, since the manipulation portion 107 is connected via the flexible cord 106 branched from the branched portion 105 at a proximal end of the inserted portion 102, only the weights of the manipulation portion 107 and flexible cord 106 are placed on the operator but not the weight of the inserted portion 102. Besides, the manipulation portion 107 includes only the angle manipulation portion 116 and its accessories, the air and water supply switch 117a, and the suction switch 117b and none of the illuminating optical system, air and water supply line, suction, line, and signal line that are relatively heavy pass through the manipulation portion 107. As a result, the manipulation portion 107 has such a small size and weight as to alleviate the fatigue of the operators left hand, thereby improving the manipulability of the endoscope.

(Twelfth Embodiment)

Figure 13:
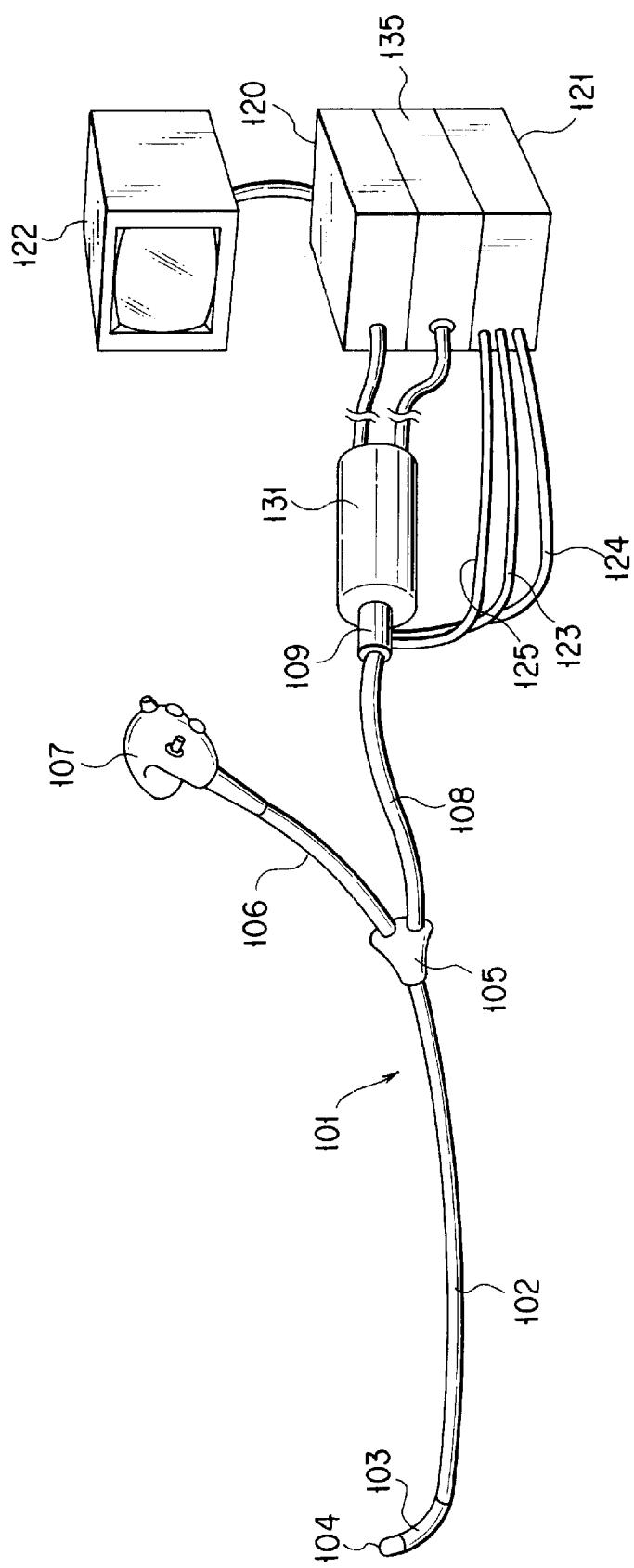
FIG. 13 is a perspective view of an endoscope device showing a twelfth embodiment of the present invention.
Figure 14:
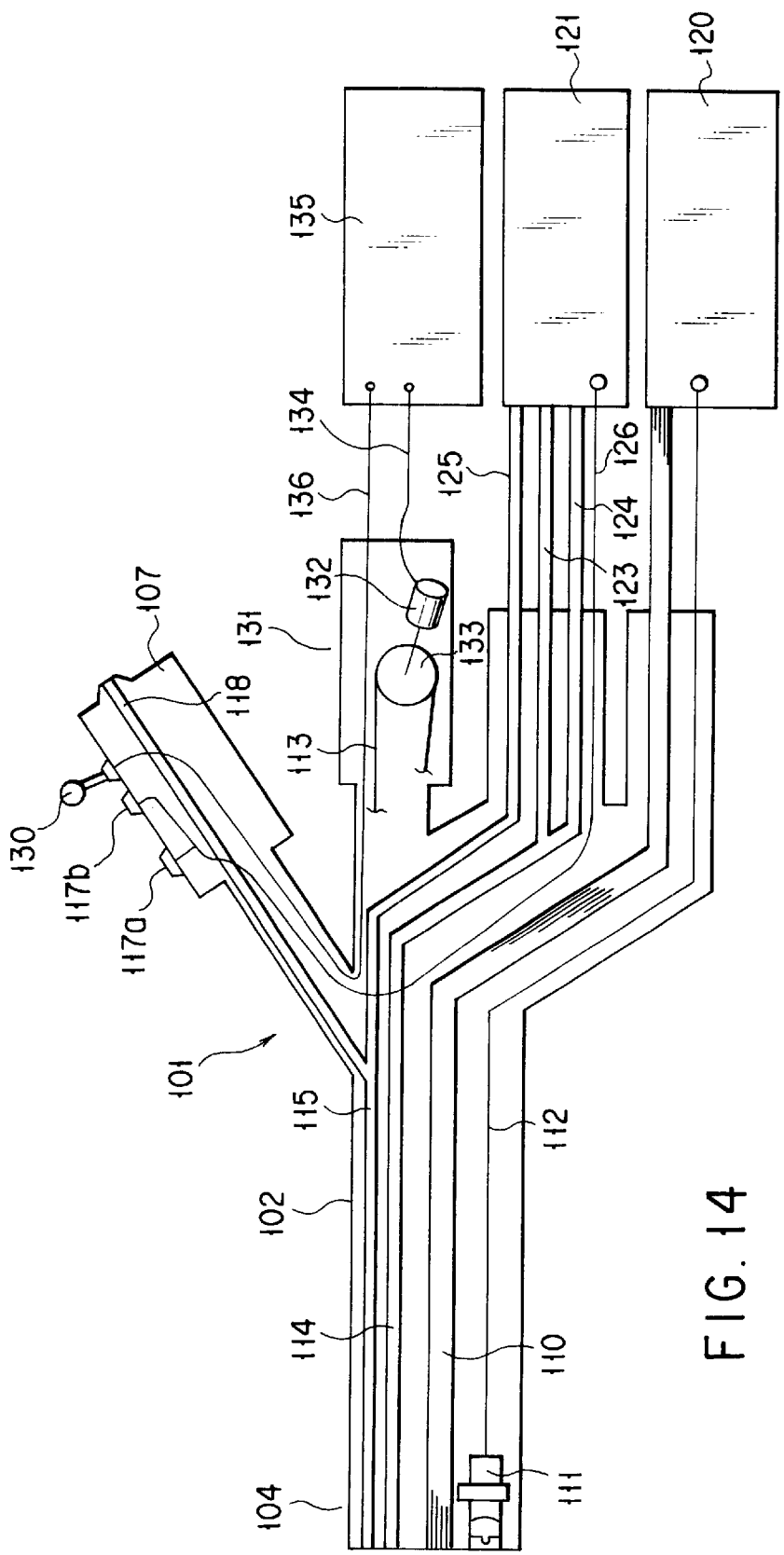
FIG. 14 is a schematic configuration diagram of the endoscope device according to the twelfth embodiment.

FIGS. 13 and 14 show a twelfth embodiment. The same components as in the eleventh embodiment have the same reference numerals, and description thereof is omitted. FIG. 13 is a perspective view of the overall endoscope device, and FIG. 14 is a configuration diagram of the overall endoscope device. One of the branches from a branched portion 105 provided at a proximal end of an inserted portion 102 has a manipulation portion 107 connected thereto via a flexible cord 106, while the other branch from the branched portion 105 has a connector 109 connected thereto via a universal cord 108.

The manipulation 107 has a curving manipulation switch 130 acting as a curving manipulation portion, an air and water supply switch 117a and a suction switch 117b, and a treatment instrument insertion port 118 in communication with a forceps channel 115.

The connector 109 can be attached and detached to and from a motor unit 131 having a motor 132 for forward and backward rotations and a rotating drum 133 rotated by the motor 132. The rotating drum 133 has an angle wire 113 laid around it and which can be pushed and pulled to curve the curved portion 103. Although the motor unit 131 is shown with one set of the angle wire 113, the motor 132, and the rotating drum 133, two sets are actually provided to enable the curved portion 103 to be curved both in a vertical and a lateral directions. The motor 132 is connected via a cord 134 to a motor control unit 135 operating as an external device and connected to the curving manipulation switch 130 of the manipulation switch 107 via a cord 136.

A light source video unit 120 operating as an external device has the illuminating optical system 110 and the signal line 112 of the solid image pickup element 111 removably connected thereto. In addition, the connector 109 has an air supply line 123, a water supply line 124, and a suction line 125 connected thereto and to an air and water supply and suction unit 121. The air and water supply and suction unit 121 has a signal line 126 connected thereto and to the air and water supply switch 117a and the suction switch 117b.

The operation of the twelfth embodiment is similar to that of the eleventh embodiment, but according to the twelfth embodiment, the manipulation portion 107 is free from the angle manipulation portion 116 and its accessories and the motor unit 131, which operates as an external device, can curve the curved portion 103. Consequently, the size of the manipulation portion 107 can further be reduced to ease the operator's fatigue, thereby improving the manipulability of the endoscope.

(Thirteenth Embodiment)

Figures 15A, 15B:
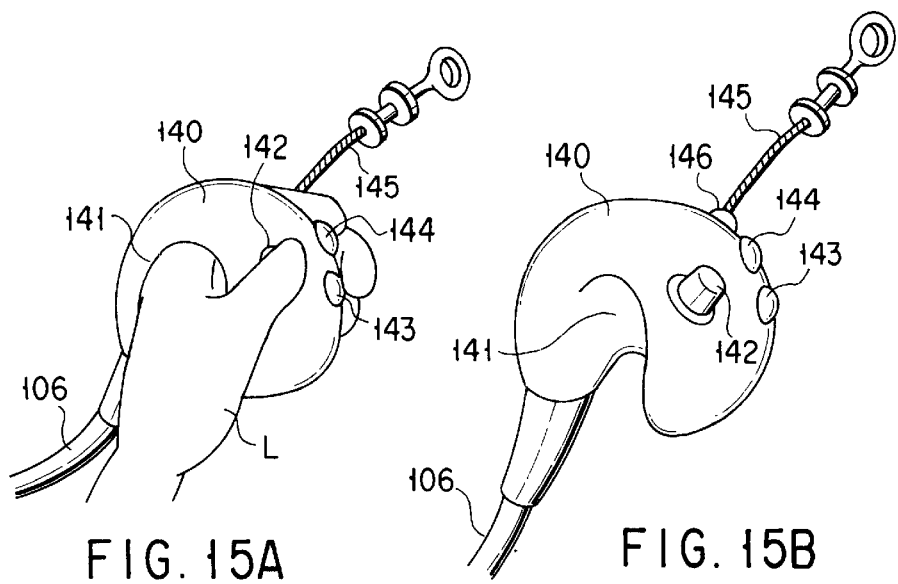
FIG. 15A is a perspective view showing that a manipulation portion according to a thirteenth embodiment of the present invention is gripped with the left hand.
FIG. 15B is a perspective view of the manipulation portion according to the thirteenth embodiment.

FIGS. 15A and 15B show a thirteenth embodiment. FIG. 15A is a perspective view showing that a manipulation portion 140 is gripped with the left hand, and FIG. 15B is a perspective view of the manipulation portion 140. The manipulation portion 140 is provided at a proximal end of a flexible cord 106 branched from a branched portion 105 as in the eleventh and twelfth embodiments. The manipulation portion 140 is generally inverted-U-shaped and has an inverted-U-shaped recess 141 provided in a lower part thereof.

The manipulation portion 140 has a curve control switch 142 operating as a curving manipulation portion, an air and water supply switch 143, and a suction switch 144 that are all provided on an outer right side surface thereof and has a forceps hole 146 provided on a proximal-end surface for inserting a forceps 145 therethrough. By setting the left hand L in the manipulation portion 140 in such a manner that the thumb is located above the other four fingers while these four fingers are in contact with one another, the four fingers including the back of the hand are accommodated in the recess 141 of the manipulation portion 140, thereby enabling the manipulation portion 140 to be held without the need to grip it. Then, the thumb, the forefinger, and the middle finger can be used to operate the curve control switch 142, the suction switch 144, and the air and water supply switch 143, respectively.

According to the manipulation portion 140 of the thirteenth embodiment, the operator can hold the manipulation portion 140 without the need to firmly grip it, whereby the operator's fatigue can be relieved to improve the manipulability of the endoscope.

(Fourteenth Embodiment)

Figures 16A, 16B:
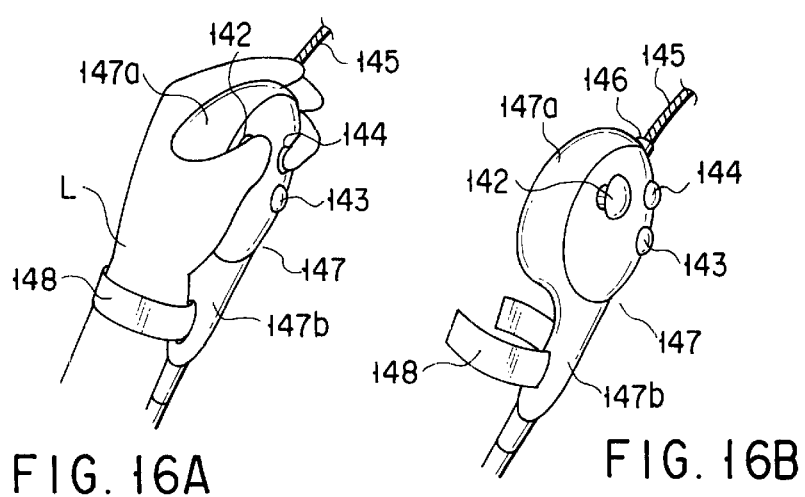
FIG. 16A is a perspective view showing that a manipulation portion according to a fourteenth embodiment of the present invention is fixed to the left hand.
FIG. 16B is a perspective view of the manipulation portion according to the fourteenth embodiment.

FIGS. 16A and 16B show a fourteenth embodiment. FIG. 16A is a perspective view showing that a manipulation portion 147 is fixed to the left hand, and FIG. 16B is a perspective view of the manipulation portion 147. The manipulation portion 147 is provided at a proximal end of a flexible cord 106 branched from a branched portion 105 as in the eleventh and twelfth embodiments. The manipulation portion 147 has a proximal end portion formed into a general sphere and a tip portion 147b formed into a flat shape integral with the proximal end portion 147a, and the tip portion 147b has a belt 148 that is fixed to the wrist of the operator's left hand L.

In addition, the manipulation portion 147 has a curve control switch 142 operating as a curving manipulation portion, an air and water supply switch 143, and a suction switch 144 that are all provided on an outer right side surface of the proximal end portion 147a and has a forceps hole 146 provided on a proximal-end surface for inserting a forceps 145 therethrough.

By fixing the manipulation portion 147 to the left hand L using the belt 148, generally the entire proximal end portion 147a of the manipulation portion 140 can be gripped by the palm. Then, the thumb, the ring finger, and the little finger can be used to operate the curve control switch 142, the suction switch 144, and the air and water supply switch 143, respectively.

According to the manipulation portion 147 of the fourteenth embodiment, the operator can hold the manipulation portion 147 without the need to firmly grip it. In manipulating manipulation means other than the manipulation portion 147 during a procedure, the operator can perform a series of operations without the need to release the manipulation portion 147 from the left hand L, whereby the manipulability of the endoscope can be improved.

(Fifteenth Embodiment)

Figures 17A, 17B:
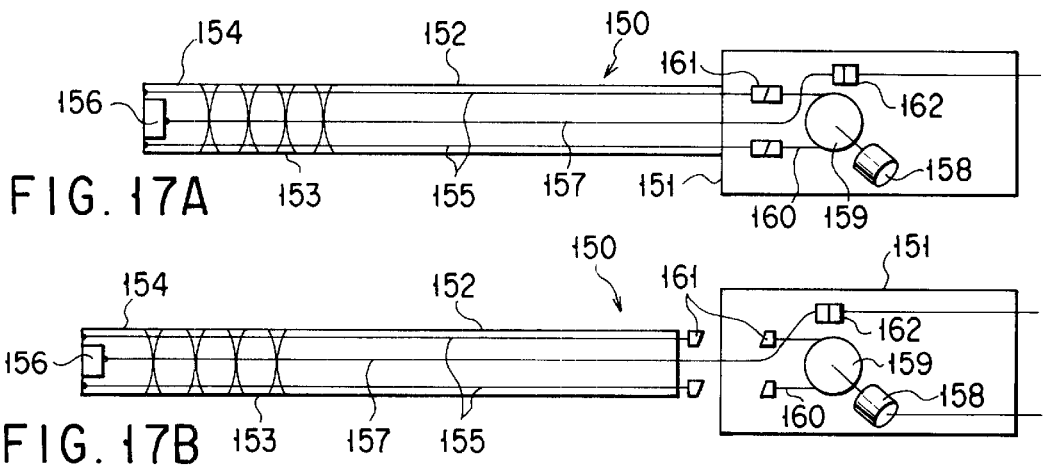
FIGS. 17A and 17B are schematic configuration diagrams of an endoscope showing a fifteenth embodiment of the present invention respectively.

FIGS. 17A and 17B show a fifteenth embodiment. FIG. 17A is a schematic configuration diagram of an endoscope and FIG. 17B is a schematic configuration diagram showing that an inserted and a manipulation portions are separated from each other. An endoscope 150 according to this embodiment consists of a manipulation portion 151 and an inserted portion 152 that can be attached and detached to and from the manipulation portion 151, and the inserted portion 152 has a tip constituting portion 154 provided on a distal end side of thereof via a curved portion 153.

The curved portion 153 has an inserted-portion-side angle wire 155 extending to the manipulation portion 151, and the tip constituting portion 154 has a solid image pickup element 156. The solid image pickup element 156 has a signal line 157 extending to the manipulation portion 151.

There is provided inside the manipulation portion 151 a motor 158 and a rotating drum 159 rotated by the motor 158, and the rotating drum 159 has a manipulation-portion-side angle wire 160 laid around it. The manipulation-portion-side angle wire 155 has opposite ends each connected to a corresponding one of the opposite ends of the manipulation-portion-side angle wire 160 by means of an angle wire connector 161. Further, the manipulation portion 151 has the signal line 157 of the solid image pickup element 156 drawn thereinto, where the signal line 157 is connected to a signal connector 152 connected to a light source video unit (not shown).

Furthermore, the signal line 157, which is guided out from a proximal end of the inserted portion 152 and connected to a signal line connector 162, has a larger length than the manipulation angle wire 155, which is guided out from the proximal end of the inserted portion 152 and connected to the angle wire connector 161.

Thus, if a curving operation is inappropriate, for example, if the curved portion 153 stops in a curved state due to a failure in the motor 158 or runs uncontrollably, the curving operation is stopped by separating the inserted portion 152 from the manipulation portion 110 to disconnect the angle wire connector 161. Since, however, the signal line 157 remains connected, the inserted portion 152 can be pulled out while checking the inside of the body cavity using a monitor (not shown).

(Sixteenth Embodiment)

FIGS. 18A to 18C show a sixteenth embodiment. The same components as in the twelfth embodiment have the same reference numerals, and description thereof is omitted. A flexible cord 106 branched from an inserted portion 102 via a branched portion 105 has an air supply line 123, a water supply line 124, and a suction line 125 inserted therethrough and connected to an air and water supply and suction unit 121 after penetrating a manipulation portion 107.

The manipulation portion 107 has a through-hole 163 independently penetrated by the air supply line 123, the water supply line 124, and the suction line 125. A support hole 164 is formed in an upper part of the manipulation portion 107 in such a manner as to be opposed perpendicularly to the through-hole 163, and the support hole 164 has a push button 165 inserted thereinto for free advancement and retreat. The push button 165 usually remains pushed up by means of the elasticity of soft tubes constituting the lines as shown in FIG. 18B, but depressing the push button by the hand or finger enables the soft tubes to collapse to occlude the lines as shown in FIG. 18C.

Thus, since a situation is dangerous in which air or water supply or suction is unintentionally continued due to a failure in a pump or solenoid valve in the air and water supply and suction unit 121, the air or water supply or suction can be stopped by depressing the push button 165 to occlude the lines, thereby improving safety.

(Seventeenth Embodiment)

Figure 19:
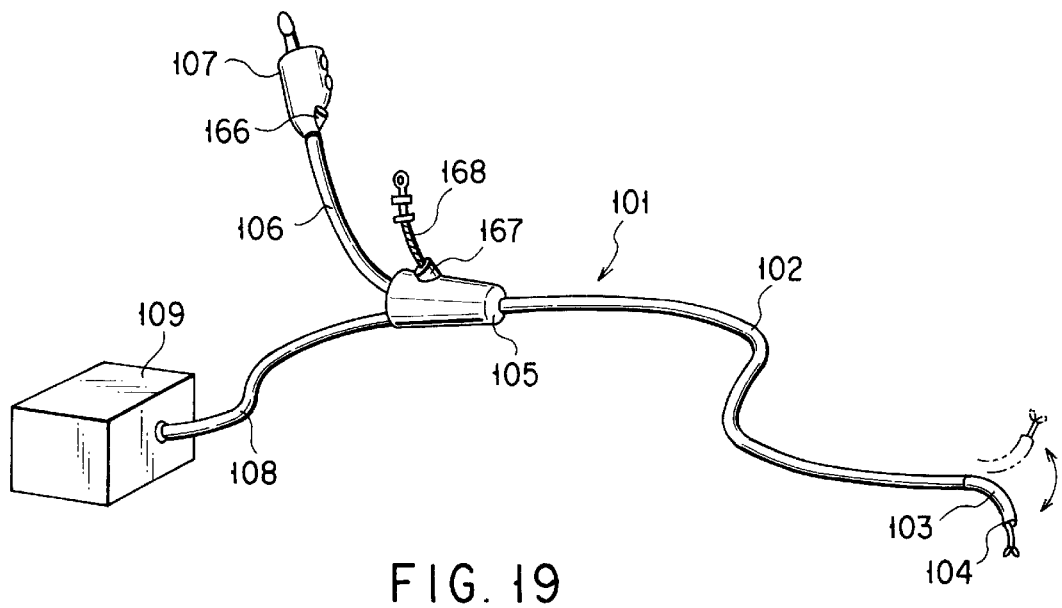
FIG. 19 is a perspective view of an endoscope device showing a seventeenth embodiment of the present invention.

FIG. 19 shows a seventeenth embodiment. The same components as in the twelfth embodiment have the same reference numerals, and description thereof is omitted. A flexible cord 106 branched from an inserted portion 102 via a branched portion 105 includes a manipulation portion 107 having a first forceps hole 166 formed therein, and the branched portion 105 has a second forceps hole 167 formed therein.

The operator typically grips the manipulation portion 107 with the left hand and inserts a forceps through the first forceps hole 166 to gather tissues as required, and an assistant such as a nurse often stands between the manipulation portion 107 and the inserted portion 102 to assist the operator in manipulation. In this case, following the operator's instructions, the assistant can insert a forceps 168 through the second forceps hole 167, which is provided in the branched portion 105. Consequently, the operator and the assistant are prevented from coming in contact with each other, whereby the manipulability of the endoscope can be improved.

(Eighteenth Embodiment)

Figure 20:
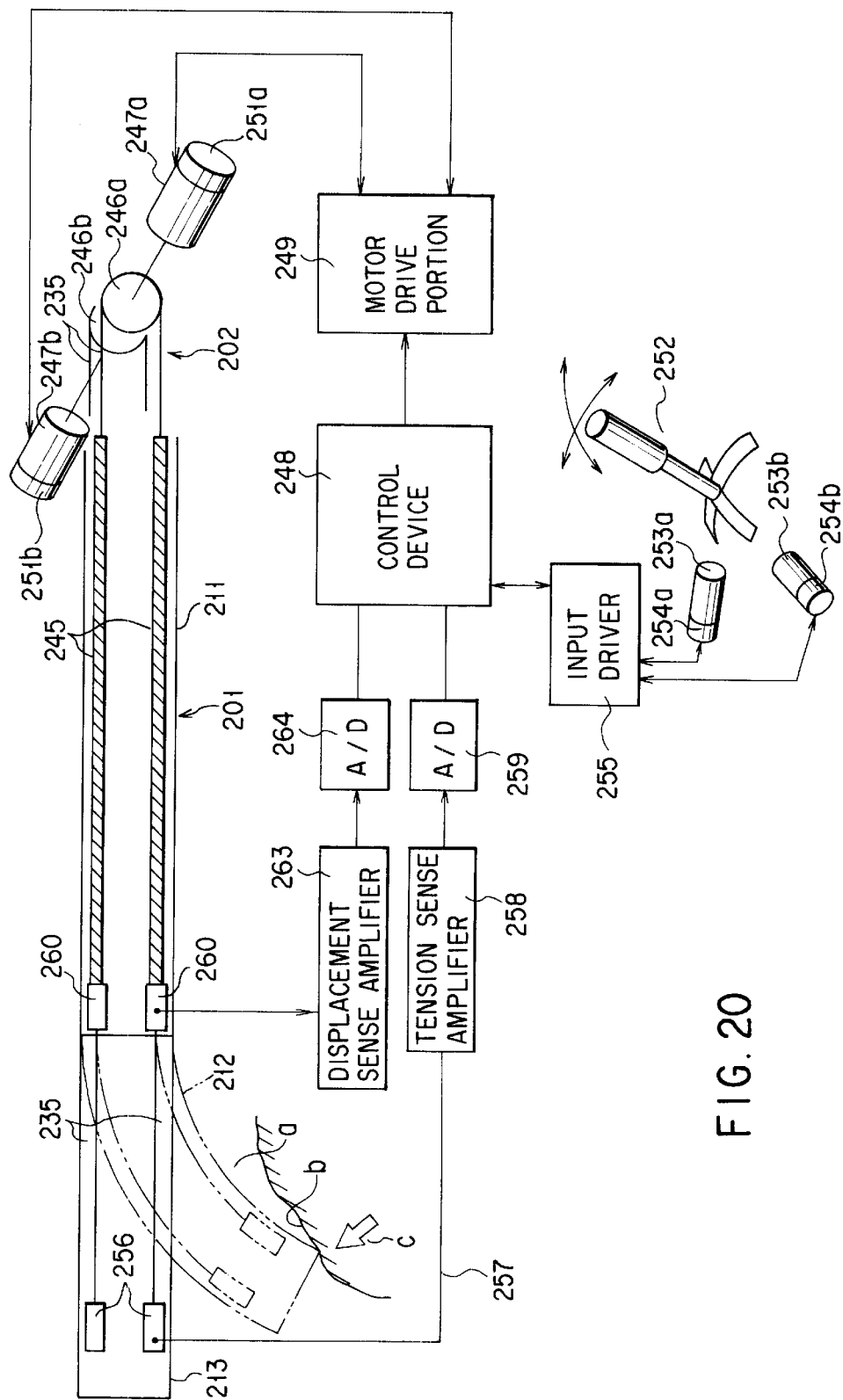
FIG. 20 is a schematic configuration diagram of a motor-operated curved endoscope according to an eighteenth embodiment of the present invention.

FIG. 20 is a schematic configuration diagram showing a configuration of a motor-operated curved endoscope. An electronic soft endoscope has a manipulation portion 202 connected to an inserted portion 201 thereof on its side closer to the operator than to the patient. The inserted portion 201 is comprised of an elongate flexible tube portion 211, a curved tube portion 212 connected to a tip of the flexible tube portion 211, and a hard tip portion 213 connected to a tip of the curved tube portion 212. The tip portion 213 has a solid image pickup element 214 such as a CCD and other devices provided therein as shown in FIG. 21.

Figure 21:
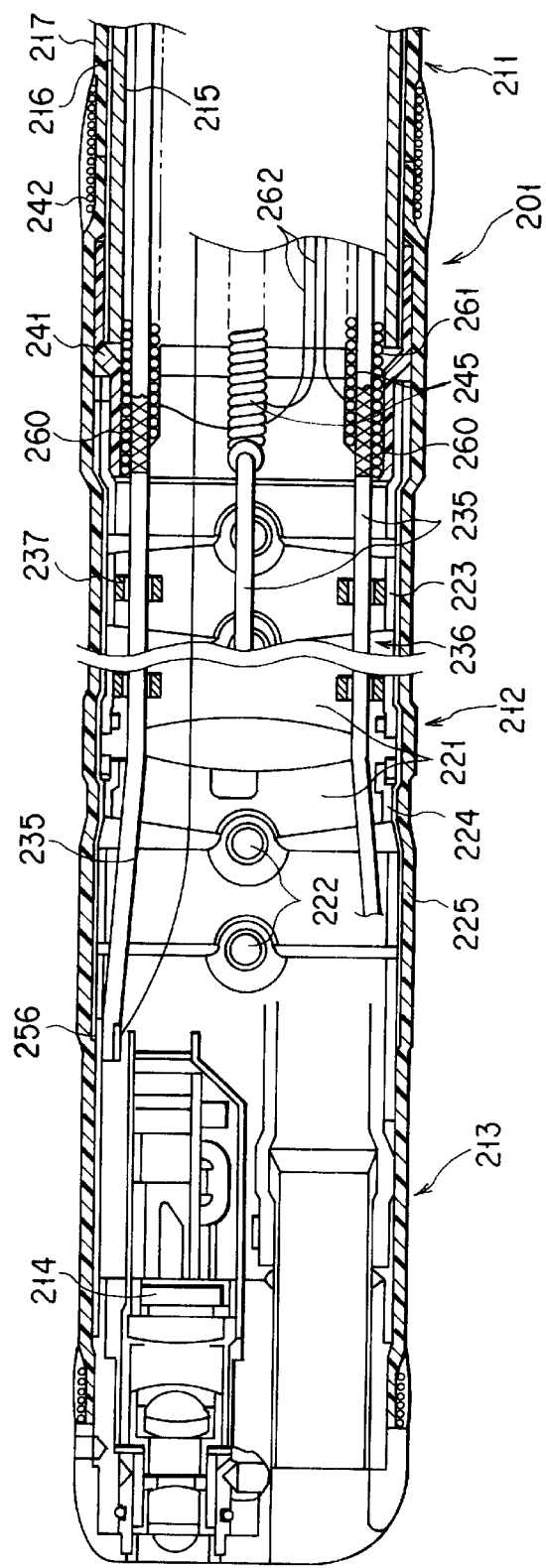
FIG. 21 is a vertical sectional view of a flexible tube portion and a curved tube portion both located in an inserted portion of the endoscope according to the eighteenth embodiment.

The flexible tube portion 211 is constructed by fitting a braid tube 216 on a spiral tube 215 and covering the braid tube 216 with a casing 217 as shown in FIG. 21. The spiral tube 215 is formed into a cylinder by winding a band-shaped metallic plate in the form of a spiral, and the braid tube 216 is formed into a cylinder by braiding a large number of metallic wires.

As shown in FIG. 21, the curved tube portion 212 has a plurality of curved blocks 221 arranged in a longitudinal axial direction of the inserted portion 201; the curved tube portion 212 is configured by using rivet-like shaft pins 222 to rotatably connecting the adjacent curved blocks 221 together to construct an entirely bendable tubular curved tube core 223, fitting a cylindrical braid on the curved tube core 223 in an outer periphery thereof, and covering an outer periphery of the braid 224 with a casing 225. The curving direction of the individual curved blocks 221 depends on positions at which the shaft pins 222 are provided. In this case, the shaft pins 222 are arranged alternately or as appropriate in a lateral or vertical direction so as to enable the curved tube core 223 to be entirely curved in the lateral or vertical direction. The curved tube core 223 constitutes a curving mechanism 236 that is curved in a traction direction by means of an angle wire 235, which will be described below.

In addition, the curved blocks 221 other than the leading and trailing ones 221 each have ring-shaped wire guides 237 attached by means of brazing or the like to an inner surface thereof at positions corresponding to the angle wires 235, which are arranged in an upper and a lower positions as well as a left and a right positions, so that the angle wires 235 can be individually inserted through these curved blocks 221 and guided for free advancement and retreat. The leading curved block or the body member of the tip portion 213 has tips of the angle wires 235 each fixed thereto by means of brazing or the like.

By selecting and drawing one of the angle wires 235, the curved tube portion 212 can be curved in the direction of the selected angle wire 235.

The flexible tube portion 211 and curved tube portion 212 of the inserted portion 201 are connected together using a metallic connection tube 241. The spiral tube 215 and braid tube 216 of the flexible tube portion 211 have a laminated tip portion fitted in a rear end portion of the connection tube 241 and fixed thereto by means of brazing or the like. In addition, a rear end portion of the trailing curved block 221 in the curved tube core 223 of the curved tube portion 212 is fitted on an outer periphery of a tip portion of the connection tube 241 and fixed by means of brazing or screwing.

Rear end portions of the braid 224 and casing 225 of the curved tube portion 212 pass beyond the trailing curved block 221 to the outer peripheral portion of the connection tube 241, where these portions are fitted and fixed by means of brazing or the like. The casing 217 of the flexible tube portion 211 and the casing 225 of the curved tube portion 212 are butted on each other, and a yarn 242 is tightly wound and tightened around the butted end portions thereof on their outer periphery. Then, an adhesive 243 is applied to an outer periphery of the yarn-wound portion to seal the butted portion in a liquid-tight manner. Such a connection portion between the flexible tube portion 211 and the curved tube portion 212 typically constitutes a relatively hard area.

Each of the angle wires 235 is individually inserted through a corresponding guide sheath inside the flexible tube portion 211 and is guided into the manipulation portion 202. The guide sheath consists, for example, of a coil sheath 245 formed by tightly winding a coil wire of stainless steel (SUS) in the form of a coil, and each coil sheath 245 has a corresponding one of the angle wires 235 individually inserted therethrough. A tip of the coil sheath 245 is brazed and fixedly attached to an inner surface of the connection tube 241. A rear end side of the coil sheath 245 is located in the flexible tube portion 211 of the inserted portion 201 and guided to the manipulation portion 202 together with other built-in components.

On the other hand, as shown in FIG. 20, the manipulation portion 202 internally has a pulley 246a around which is wound a wire having each of the upper and lower angle wires 235 connected to a corresponding one of the opposite ends thereof, and a pulley 246b around which is wound a wire having each of the left and right angle wires 235 connected to a corresponding one of the opposite ends thereof. The pulleys 246a, 246b are rotated by electric motors 247a, 247b in a forward and a backward directions. The electric motors 247a, 247b are driven by a motor drive portion 249 controlled by a control device 248.

An actuator makes the electric motors 247a, 247b rotate the pulleys 246a, 246b and curves the curved tube portion 212 via the angle wire 235.

The operating position of the actuator is detected by actuator position detection means. The actuator position detection means in this embodiment is comprised of rotary encoders 251a, 251b mounted on shaft positions of the electric motors 247a, 247b so as to detect the curving angle of the curving mechanism 236 based on output signals from the rotary encoders 251a, 251b. The control device 248 is adapted to control the amount of curving manipulation performed by the actuator so as to curve the curved tube portion 212 up to a predetermined curving angle based on a position detection signal from the actuator position detection means.

That is, the manipulation portion 202 has a joy stick 252 operating as a curving manipulation portion. The joy stick 252 is used to specify a vertical and a lateral curving directions and to indicate the amount of curving manipulation. By specifying the vertical and a lateral curving directions and indicating the amount of curving manipulation, a vertical-direction joy stick motor 253a and a lateral-direction joy stick 253b are rotated, and their rotating angles, that is, the amounts of curving manipulation are detected by rotary encoders 254a, 254b. Detection signals from the rotary encoders 254a, 254b are input to the control device 248 via an input driver 255.

Next, means for detecting the state of the curved tube portion 212 will be explained.

As shown in FIG. 21, the inserted portion 201 has a tension sensor 256 such as a distortion sensor fixed to a tip portion 213 thereof in a fashion corresponding to each angle wire 235, and the tension sensor 256 has a tip portion of the angle wire 235 connected thereto to detect the tension of the angle wire 235. A signal line 257 from the tension sensor 256 is connected to the control device 248 through the inserted portion 201 via a tension sense amplifier 258 and an A/D converter 259 both provided in the manipulation portion 2.

Furthermore, a displacement sensor 260 such as an electromagnetic induction sensor or a laser displacement sensor is fixed to the inside of the connection tube 241 between the tip portion of the flexible tube portion 211 and the rear end portion of the curved tube portion 212 to detect the displacement of the angle wire 235 in its axial direction. The displacement sensor 260 is integrated into a coil sheath 245 through which the angle wire 235 is inserted and guided. Signal lines 262 are guided out from opposite ends of a sensor coil 261 of the displacement sensor 260 and connected to the control device 248 through the inserted portion 201 via a displacement sense amplifier 263 and an A/D converter 264 both provided in the manipulation portion 202.

Next, the operation of the eighteenth will be described. When the joy stick 252 is rotatively moved, for example, in a vertical direction of the operator, the joy stick motor 253a rotates and its rotation is detected by the encoder 254a, which then inputs an instruction to the control device 248 via the input driver 255. Then, the electric motor 247a rotates the pulley 246a in a rotating direction of the motor to draw the angle wire 235 so as to curve the curved tube portion 212 in a desired direction. At this point, the electric motor 247a is servo-controlled.

Figure 22:
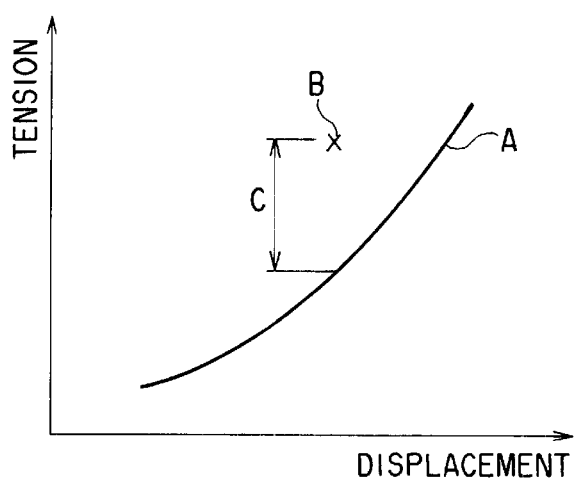
FIG. 22 is an explanatory drawing showing the operation of the eighteenth embodiment.

In this case, as shown in FIG. 22, without an external force applied to the curved tube portion 212, the tension measured by the tension sensor 256 increases linearly with the displacement measured by the displacement sensor 260 as indicated by a curve A. If, however, the relationship between the tension measured by the tension sensor 256 and the displacement measured by the displacement sensor 260 is determined at a point B during actual curving of the curved tube portion 212 or during a medical treatment, then an external force corresponding to a difference in tension C relative to the curve A is being applied to the curved tube portion 212.

That is, as shown in FIG. 20, if the inserted portion 201 is inserted into a body cavity a and the curved tube portion 212 is curved, the displacement of the angle wire 235 is measured by the displacement sensor 260, and results of the measurement are input to the control device 248 via the displacement sense amplifier 263 and the A/D converter 264. In addition, when the curved tube portion 212 is curved and if the tip portion 213 abuts on a body cavity wall b to further curve the curved tube portion 212 or if an external force is applied from the body cavity wall b in the direction indicated by an arrow c, then the tension sensor 256 measures this tension and results of the measurement are input to the control device 248 via the tension sense amplifier 258 and the A/D converter 259. The control device 248 calculates the difference in tension C relative to the curve A and operates the input driver 255 so as to feed back to the joy stick 252 an amount of force corresponding to the value C. Accordingly, the operator manipulating the joy stick 252 senses in the hand an external force applied to the tip portion 213 of the inserted portion 201.

According to the above embodiment, with the displacement sensor 260 installed in the inserted portion 201 to measure the displacement of the angle wire, reliable control can be provided so as to avoid the angle down phenomenon despite deformation of the inserted portion 201. In addition, with the tension sensor 256 installed to measure the tension of the angle wire 235, when the curved tube portion 212 is curved and the tip portion 213 then abuts on the body cavity wall b or the like to apply an external force to the curved tip portion 212, the tension is measured by the tension sensor 256.

Further, since the controller 248 calculates the difference in tension C and feeds back to the joy stick 252 an amount of force corresponding to the difference C, the operator manipulating the joy stick 252 senses in the hand an external force applied to the tip portion 213 of the inserted portion 201. Thus, joy stick 252 can be used for manipulations such as returning the curved tube portion 212 to a straight form and changing the curving direction, thereby improving the manipulability of the endoscope.

The present invention, however, is not limited to the above configuration in which the tension sensor 256 measures the tension of the angle wire 235 so that the control device 248 can calculate the difference in tension C and feeds back to the joy stick 252 a amount of force corresponding to the difference C. For example, the operator may be notified of an external force applied to the tip portion 213 by means of lighting of an alarm lamp or actuation of an alarm buzzer based on a detection signal from the tension sensor 256.

Although the above embodiment uses the electric motor as drive means for drawing the angle wire 235, another actuator may be used.

Furthermore, the present invention is not limited to medical endoscopes but is applicable to industrial ones. In particular, for an industrial endoscope searching a pipe line, in curving the curved tube portion of the inserted portion, the operator may continue moving the inserted portion forward without noticing that the tip portion is abutting the pipe wall, thereby cutting the angle wire or damaging the curved tube portion or the tip portion of the curved tube portion. This problem can be solved by providing the tension sensor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope holder comprising:
   an arm member including a holding portion near a distal end portion of said arm member for holding an endoscope such that an inserted portion of the endoscope is extended downward, said holding portion holding a proximal end portion of the endoscope from a direction that intersects with a longitudinal axis of the inserted portion;
   a rotating member arranged in the holding portion for rotating the endoscope held by the holding portion around the longitudinal axis of the inserted portion; and
   a manipulation portion, which is provided on the distal end portion of the arm member such that the manipulation portion extends away from the arm member beyond the holding portion, for manipulating the endoscope held by the holding portion;
   wherein the endoscope held by the holding portion is rotated by the rotating member with respect to the manipulation portion around the longitudinal axis of the inserted portion.

2. An endoscope holder according to claim 1, wherein said holding portion is suspended from a control box having a light source video unit and an air and water supply and suction unit.

3. An endoscope holder according to claim 2, wherein said control box is installed on a ceiling.

4. An endoscope holder according to claim 2, wherein said control box is installed on a horizontal portion of a frame.

5. An endoscope holder according to claim 2, wherein said control box comprises a built-in housing device around which a flexible tube is wound for delivery, and wherein the flexible tube comprises a light guide fiber, a signal line, an air and water supply and a suction tube.

6. An endoscope holder according to claim 5, wherein said housing device comprises a gravity balancer for urging said flexible tube in a winding direction.

7. An endoscope holder according to claim 1, wherein said holding-portion has an articulated structure, and wherein an articulated portion of the holding portion has an electromagnetic clutch brake.

8. An endoscope holder according to claim 1, wherein said holding portion has a gravity balancer for balancing the endoscope.

9. A medical apparatus comprising:
   an endoscope;
   an endoscope holder having a holding portion for rotatably supporting the endoscope such that an inserted portion of the endoscope is extended downward; and
   a manipulation portion for manipulating the endoscope;
   wherein said endoscope holder is provided on one armrest portion of a chair and said manipulation portion is provided on another armrest portion of the chair.

10. A medical apparatus comprising:

an endoscope;

an endoscope holder having a holding portion for rotatably supporting the endoscope such that an inserted portion of the endoscope is extended downward;

wherein the endoscope comprises a manipulation portion connected to the inserted portion;

wherein said inserted portion comprises a branched portion at a proximal end thereof, wherein the manipulation portion comprises a curving manipulation portion, and wherein the curving manipulation portion is provided on a first one of the branches of the branched portion via a flexible cord, and a second one of the branches has external devices connected thereto via a universal cord.

11. A medical device according to claim 10, wherein said external devices are a light source video unit, an air and water supply unit and suction unit, and a motor control unit.

12. A medical device according to claim 11, wherein the air and water supply and suction line are inserted through the manipulation portion, and wherein the manipulation comprises means for blocking said line.

13. A medical device according to claim 10, wherein said flexible cord comprises at least a signal line and a forceps channel, and wherein said universal cord comprises at least a signal line and an air and water supply and suction line.

14. A medical device according to claim 10, wherein said manipulation portion and said inserted portion of the endoscope are adapted to be disconnected from each other together with angle wires and signal lines, and wherein the signal lines are set to be longer than the angle wires.

15. A medical device according to claim 10, wherein said manipulation portion comprises a first forceps hole formed therein, and wherein said branched portion has a second forceps hole formed therein.

16. A medical device according to claim 10, wherein:

said inserted portion comprises a curved tube portion including a curving mechanism and angle wires inserted therethrough for curving the curving mechanism, said manipulation portion comprises an actuator for drawing said angle wires to manipulate said curving mechanism so as to curve said curved tube portion, and said curving manipulation portion controls said actuator, and wherein the endoscope comprises control means for detecting a state of said curved tube portion based on sensor outputs from a tension sensor for detecting tension of said angle wires and a displacement sensor for detecting displacement of said angle wires.

17. A medical device according to claim 16, wherein said tension sensor is provided at a tip portion of said inserted portion in correspondence with the angle wires and has a tip portion of the angle wires connected thereto.

18. A medical device according to claim 16, wherein said displacement sensor is provided at a tip portion of a flexible tube portion of said inserted portion in correspondence with the angle wires and has a middle portion of the angle wires inserted therethrough.

19. A medical device according to claim 16, wherein said control means calculates a difference between a tension detected by the tension sensor and a tension measured during normal curving, and feeds back to said curving manipulation portion a force corresponding to the difference.

* * * * *